US010675431B2

(12) United States Patent
Klasek

(10) Patent No.: US 10,675,431 B2
(45) Date of Patent: Jun. 9, 2020

(54) METHODS AND APPARATUS FOR IONIZATION

(71) Applicant: ResMed Pty Ltd, Bella Vista, NSW (AU)

(72) Inventor: Paul Jan Klasek, Bonnyrigg Heights (AU)

(73) Assignee: ResMed Pty Ltd (AU)

( * ) Notice: Subject to any disclaimer, the term of this patent is extended or adjusted under 35 U.S.C. 154(b) by 804 days.

(21) Appl. No.: 14/647,515

(22) PCT Filed: Nov. 26, 2013

(86) PCT No.: PCT/AU2013/001365
§ 371 (c)(1),
(2) Date: May 27, 2015

(87) PCT Pub. No.: WO2014/082120
PCT Pub. Date: Jun. 5, 2014

(65) Prior Publication Data
US 2015/0290416 A1 Oct. 15, 2015

Related U.S. Application Data

(60) Provisional application No. 61/777,022, filed on Mar. 12, 2013, provisional application No. 61/730,271, filed on Nov. 27, 2012.

(51) Int. Cl.
*A61M 16/10* (2006.01)
*A61M 16/00* (2006.01)
(Continued)

(52) U.S. Cl.
CPC ....... *A61M 16/1005* (2014.02); *A61B 5/0205* (2013.01); *A61B 5/087* (2013.01);
(Continued)

(58) Field of Classification Search
CPC .............. A61M 15/02; A61M 16/0003; A61M 16/0069; B03C 3/00; B03C 3/38;
(Continued)

(56) References Cited

U.S. PATENT DOCUMENTS 2,060,842 A * 11/1936 Yaglou ...................... A61L 9/22
128/202.25
2,381,455 A * 8/1945 Jacob ........................ B03C 3/383
96/16
(Continued)

FOREIGN PATENT DOCUMENTS

CN 1244961 A 2/2000
CN 1788807 A 6/2006
(Continued)

OTHER PUBLICATIONS

Extended European Search Report for Application No. 13859282.9 dated Jun. 17, 2016.
(Continued)

*Primary Examiner* — Nyca T Nguyen
(74) *Attorney, Agent, or Firm* — Botos Churchill IP Law LLP

(57) ABSTRACT

Devices and systems provide methods of controlling breathable gas generation such as for a respiratory treatment and/or for controlling ionization of the gas. In an example, a controller of a respiratory treatment apparatus controls generation of a supply of ionized air. The apparatus may include a flow generator to generate a flow of pressurized breathable gas. The flow generator may be adapted for connection with a respiratory interface. The apparatus may also include an ionizer to ionize the flow of gas. The controller may be coupled with the ionizer and the flow generator and be configured to control the ionizer to programmatically change levels of ionization of the gas. Such ionized gas treatments may be suitable for helping users to sleep or improving
(Continued)

respiratory oxygen absorption, and may be for patients with, for example, sleep disordered breathing or chronic obstructive pulmonary disease.

25 Claims, 19 Drawing Sheets

(51) Int. Cl.

| | | |
|---|---|---|
| A61M 16/06 | (2006.01) | |
| A61M 16/08 | (2006.01) | |
| A61M 15/02 | (2006.01) | |
| A61B 5/087 | (2006.01) | |
| A61B 5/08 | (2006.01) | |
| A61B 5/00 | (2006.01) | |
| A61M 16/16 | (2006.01) | |
| A61B 5/0205 | (2006.01) | |

(52) U.S. Cl.
CPC .......... *A61B 5/0826* (2013.01); *A61B 5/4809* (2013.01); *A61B 5/4812* (2013.01); *A61B 5/4818* (2013.01); *A61B 5/4839* (2013.01); *A61M 15/02* (2013.01); *A61M 16/0066* (2013.01); *A61M 16/024* (2017.08); *A61M 16/06* (2013.01); *A61M 16/0875* (2013.01); *A61M 16/105* (2013.01); *A61M 16/16* (2013.01); *A61M 16/109* (2014.02); *A61M 2016/0027* (2013.01); *A61M 2016/0039* (2013.01); *A61M 2205/502* (2013.01); *A61M 2230/04* (2013.01); *A61M 2230/10* (2013.01)

(58) Field of Classification Search
CPC  B03C 3/383; B03C 3/386; B03C 3/40; B03C 3/41; B03C 3/43; B03C 3/32; B03C 3/68; B60H 1/00564; B60H 3/0071; H01T 23/00
USPC ..................................... 128/202.25
See application file for complete search history.

(56) References Cited

U.S. PATENT DOCUMENTS

| | | | |
|---|---|---|---|
| 2,415,659 A * | 2/1947 | Steel ................ | A61M 15/02 128/202.25 |
| 2,920,622 A | 1/1960 | Steel | |
| 3,232,292 A * | 2/1966 | Schaefer ............ | A61M 15/02 128/200.14 |
| 3,653,185 A * | 4/1972 | Scott ................. | B03C 3/38 96/16 |
| 4,102,654 A | 7/1978 | Pellin | |
| 4,264,343 A * | 4/1981 | Natarajan .......... | B03C 3/38 361/230 |
| 4,539,984 A | 9/1985 | Kiszel et al. | |
| 5,245,995 A | 9/1993 | Sullivan et al. | |
| 5,381,789 A | 1/1995 | Marquardt | |
| 5,704,345 A | 1/1998 | Berthon-Jones | |
| 5,749,359 A | 5/1998 | Hansen | |
| 6,363,933 B1 | 4/2002 | Berthon-Jones | |
| 6,375,714 B1 * | 4/2002 | Rump ................. | A61L 9/22 361/235 |
| 6,398,739 B1 | 6/2002 | Sullivan et al. | |
| 6,532,957 B2 | 3/2003 | Berthon-Jones | |
| 6,635,021 B1 | 10/2003 | Sullivan et al. | |
| 6,668,563 B2 * | 12/2003 | Mirowsky ........... | B64D 13/00 315/111.91 |
| 6,770,037 B2 | 8/2004 | Sullivan et al. | |
| 6,791,815 B1 | 9/2004 | Graham | |
| 6,845,773 B2 | 1/2005 | Berthon-Jones et al. | |
| 6,951,217 B2 | 10/2005 | Berthon-Jones | |
| 7,004,908 B2 | 2/2006 | Sullivan et al. | |
| 7,080,645 B2 | 7/2006 | Genger et al. | |
| 7,141,021 B2 | 11/2006 | Sullivan et al. | |
| 7,314,046 B2 | 1/2008 | Schroeder et al. | |
| 8,985,106 B2 | 3/2015 | Armitstead | |
| 9,687,177 B2 | 6/2017 | Ramanan et al. | |
| 2001/0027790 A1 * | 10/2001 | Gieschen .......... | A61M 15/0086 128/203.15 |
| 2004/0216745 A1 * | 11/2004 | Yuen ................. | A62B 19/00 128/205.27 |
| 2005/0188987 A1 * | 9/2005 | Yuen ................. | B03C 3/32 128/202.25 |
| 2008/0163871 A1 * | 7/2008 | Bozoky ............. | A61M 15/00 128/203.27 |
| 2009/0131803 A1 | 5/2009 | Heneghan et al. | |
| 2009/0203972 A1 | 8/2009 | Heneghan et al. | |
| 2010/0140189 A1 | 6/2010 | Jensen et al. | |
| 2010/0206308 A1 | 8/2010 | Klasek et al. | |
| 2010/0307500 A1 | 12/2010 | Armitstead | |
| 2011/0146681 A1 * | 6/2011 | Jafari ............... | A61B 5/085 128/204.21 |
| 2011/0203588 A1 | 8/2011 | Armitstead et al. | |
| 2012/0179061 A1 | 7/2012 | Ramanan et al. | |
| 2012/0212876 A1 | 8/2012 | Rais et al. | |

FOREIGN PATENT DOCUMENTS

| | | |
|---|---|---|
| DE | 4408897 A1 | 11/1995 |
| EP | 1605565 A1 | 12/2005 |
| EP | 2249446 A1 | 11/2010 |
| GB | 2300814 A | 11/1996 |
| JP | 58500390 A | 10/1982 |
| JP | 03085049 A | 8/1991 |
| JP | 2005177128 A | 7/2005 |
| WO | 1982003326 A | 10/1982 |
| WO | 1996-032055 A1 | 10/1996 |
| WO | 9737708 A1 | 10/1997 |
| WO | 1998-052467 A1 | 11/1998 |
| WO | 2005087320 A1 | 9/2005 |
| WO | 2006037184 A1 | 4/2006 |
| WO | 2006047826 A1 | 5/2006 |
| WO | 2008054855 A2 | 5/2008 |
| WO | 2008145104 A2 | 12/2008 |
| WO | 2011-006206 A1 | 1/2011 |
| WO | 20120126041 A1 | 9/2012 |

OTHER PUBLICATIONS

Krueger, Albert P. et al., The Biological Mechanisms of Air Ion Action, The Journal of General Physiology, pp. 533-540, vol. 43, 1960.
SMC EMC-Ionizer-01A-UK, Ionizer Series IZ531, SMC Corporation www.smcworld.com.
International Search Report for Application No. PCT/AU2013/001365 dated Apr. 28, 2014.
International Written Opinion for Application No. PCT/AU2013/001365 dated Apr. 28, 2014.
Japanese Patent Application No. 2015-544271 Office Action dated Aug. 18, 2017.

\* cited by examiner

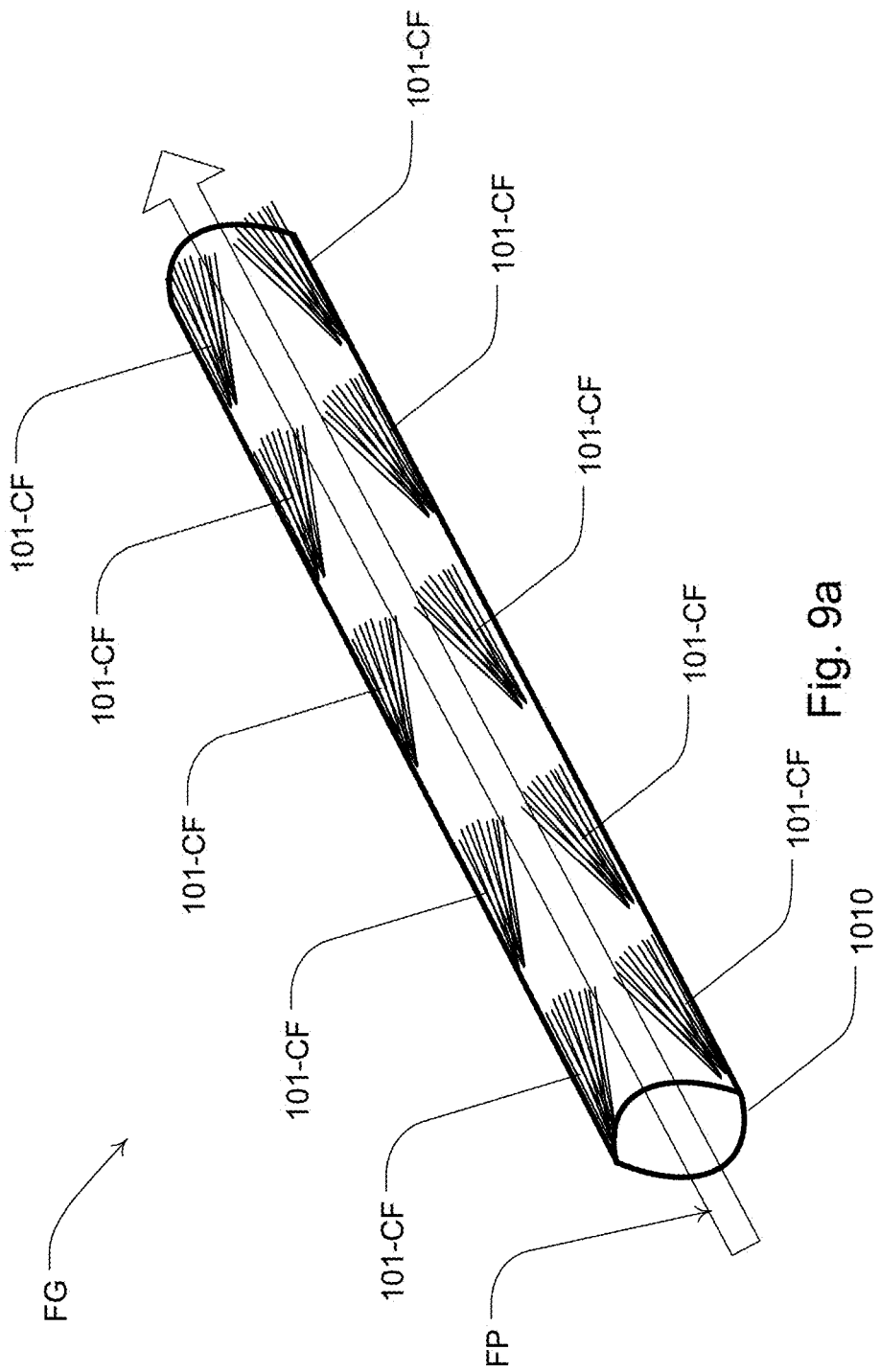

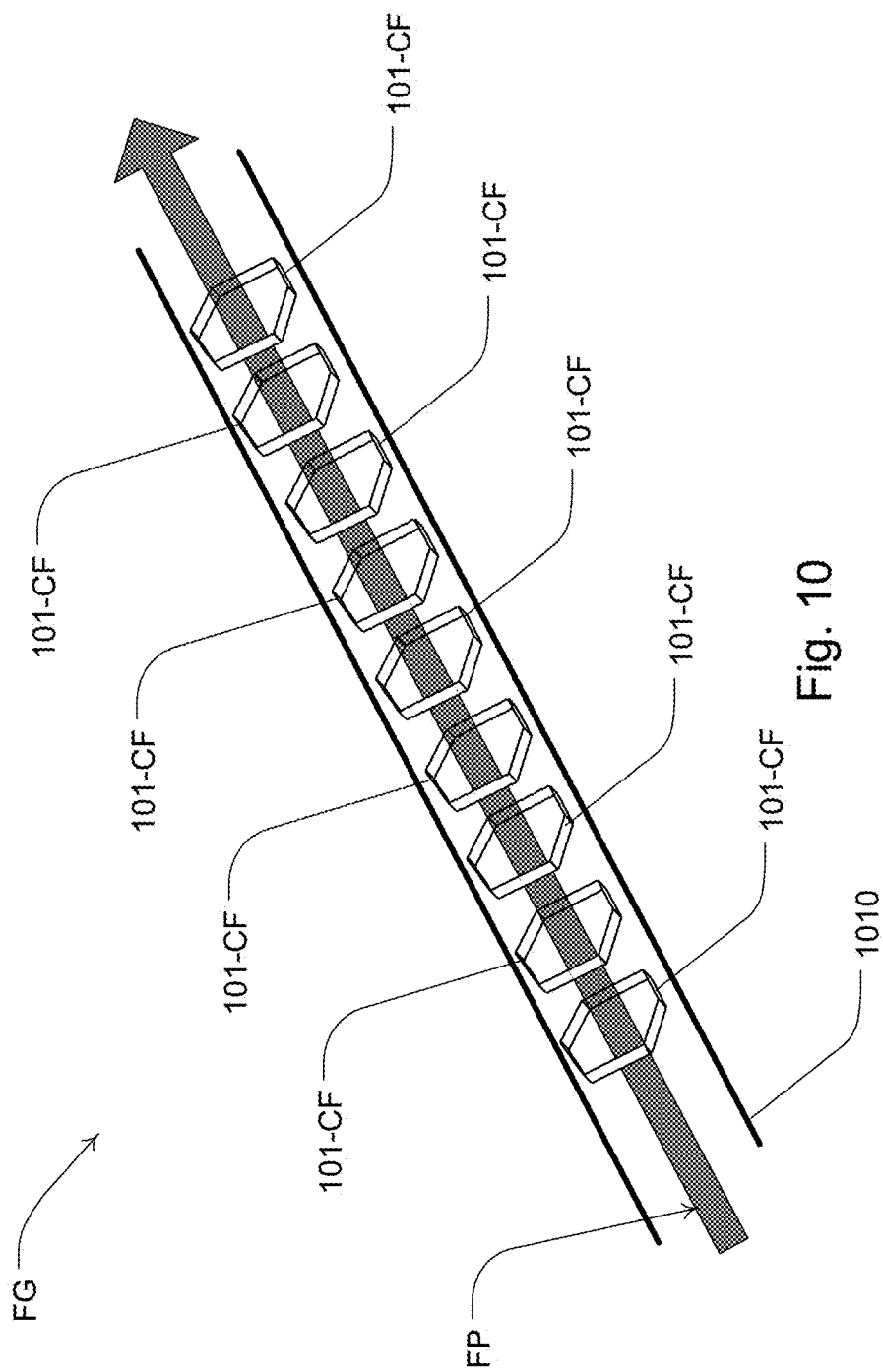

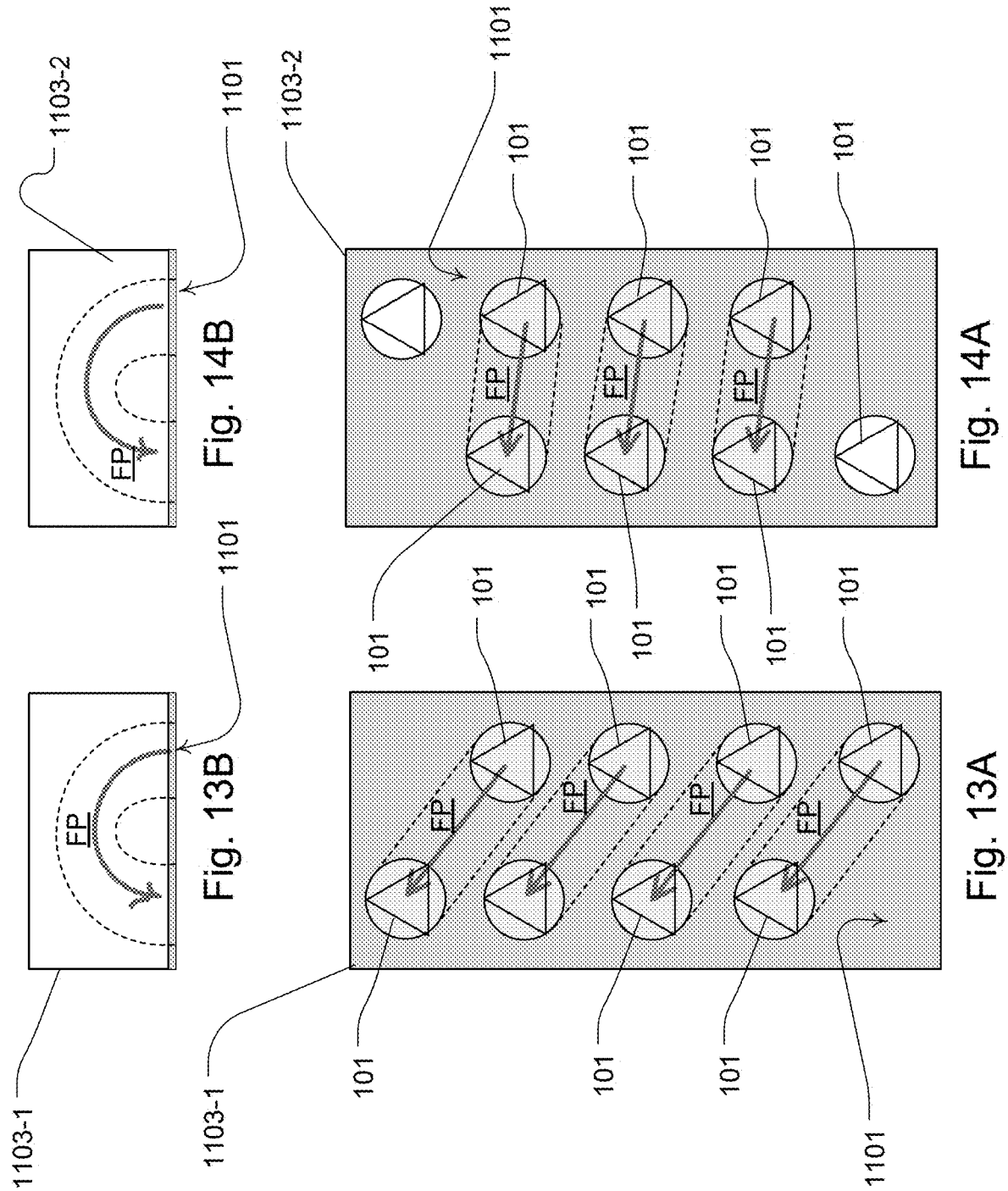

METHODS AND APPARATUS FOR IONIZATION

CROSS REFERENCE TO RELATED APPLICATIONS

The present application is a national phase entry under 35 U.S.C. § 371 of International Application No. PCT/AU2013/001365 filed Nov. 26, 2013, published in English, which claims priority from U.S. Provisional Patent Application Nos. 61/777,022 filed Mar. 12, 2013 and 61/730,271 filed Nov. 27, 2012, which are incorporated herein by reference.

FIELD OF THE TECHNOLOGY

The present technology relates to systems, methods and apparatus for treating respiratory conditions such as sleep disordered breathing or respiratory insufficiency (e.g., Chronic Obstructive Pulmonary Disease). More particularly, it relates to the ionization generation such as for ionization therapy of such conditions.

BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with SDB are also likely to disturb their partner's sleep. One known effective form of treatment for patients with SDB is nasal continuous positive airway pressure (nasal CPAP) applied by a blower (air pump or compressor) via a connecting hose and patient interface. In some forms the supply of air at positive pressure is delivered to both the nose and mouth. The positive pressure can serve as a "pneumatic splint" so as to prevent a collapse of the patient's airway during inspiration, thus preventing events such as snoring, apneas or hypopnoeas and in many cases, is effective in treating central and mixed apnea.

Such positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set, at one level during inspiration and another lower level during expiration for patient comfort. Such a pressure treatment system may be referred to as bi-level. Alternatively, the pressure levels may be continuously adjusted to smoothly change with the patient's breathing cycle. A pressure setting during expiration lower than inspiration may generally be referred to as expiratory pressure relief. An automatically adjusting device may increase the treatment pressure in response to indications of partial or complete upper airway obstruction. See U.S. Pat. Nos. 5,245,995; 6,398,739; 6,635,021; 6,770,037; 7,004,908; 7,141,021; 6,363,933 and 5,704,345.

Other devices are known for providing respiratory tract therapy. For example, Schroeder et al. describes an apparatus for delivering heated and humidified air to the respiratory tract of a human patient in U.S. Pat. No. 7,314,046, which was filed on 8 Dec. 2000 and assigned to Vapotherm Inc. Similarly, Genger et al. discloses an anti-snoring device with a compressor and a nasal air cannula in U.S. Pat. No. 7,080,645, filed 21 Jul. 2003 and assigned to Seleon GmbH.

Respiratory insufficiency affects millions of people. For patient's suffering from this condition, the lungs are unable to inspire sufficient oxygen or expel sufficient carbon dioxide to meet the needs of the cells of the patient's body. For example, Chronic Obstructive Pulmonary Disease ("COPD") affects approximately thirteen million Americans and ten million Europeans. COPD is a disease involving some damage to the lungs. The airways and the alveoli of the lungs can lose their elastic quality. Walls between alveoli can become destroyed or they can become inflamed. The airways of the lungs may also produce more mucus than usual, which can restrict airflow. This damage will typically manifest itself in some difficulty with breathing such as dyspnea. COPD patients typically experience coughing, with an expulsion of mucus, shortness of breath, wheezing and a feeling of tightness in the chest. Emphysema and chronic obstructive bronchitis may each be considered to be a form of COPD. Chronic obstructive bronchitis may be characterized by an inflammatory response in the larger airways of the lungs. Emphysema may be characterized by destruction of tissue of the lungs from an inflammatory response.

There is no presently known cure for COPD. There is no treatment for restoring the airways and alveoli of the lungs of a COPD patient to their pre-disease condition. However, treatments and lifestyle changes can help a COPD patient to feel more comfortable, continue to be active and impede the progression of the disease.

It will be appreciated that there is a need in the art for improved techniques and devices for addressing the respiratory conditions of patients such as those suffering from SDB or respiratory insufficiency such as COPD.

SUMMARY OF THE TECHNOLOGY

An aspect of certain examples of the present technology relates to methods and apparatus for controlling, generating and/or providing a respiratory treatment.

Another aspect of some examples of the present technology is the implementation of ion generators for cleaning, generating gas flow/propulsion and/or therapy for a user's respiratory system.

A further aspect of some examples of the technology relates to methods and apparatus for controlling, generating and/or providing an ionization respiratory treatment.

Another aspect of certain examples of the present technology relates to methods and apparatus for independently controlling a setting or generation of a pressurized breathable gas as a respiratory treatment and contemporaneously but independently controlling a setting or generation of an ionization of the breathable gas.

Another aspect of certain examples of the present technology is a controller for an apparatus configured to programmatically control changes to settings for generation of a pressurized breathable gas as a respiratory treatment and for controlling changes to settings for generation of an ionization of the breathable gas.

In some examples of the present technology, a respiratory treatment apparatus may be configured to generate a controlled supply of ionized breathable gas. The apparatus may include a flow generator to generate a flow of breathable gas at a pressure above atmospheric pressure. The flow generator may be adapted for connection with a patient respiratory interface. The apparatus may also include an ionizer to ionize the flow of breathable gas at a level of ionization. The apparatus may also include a controller, such as one that includes a processor. The controller may be coupled with the ionizer and the flow generator. The controller may be configured to control the ionizer to programmatically change the level of ionization of the pressurized flow of breathable gas to set the level to a plurality of different ionization levels.

In some cases, the controller may be configured to decrease the level of ionization over a period of time. The controller may be configured to increase the level of ionization over a period of time. The controller may be further configured to pulse the level of ionization over a period of time. In some cases, the controller may be configured decrease the level of ionization after expiration of a wake period.

Optionally, the apparatus may also include a sensor coupled with the controller. The sensor may be configured to detect a physiological characteristic. The controller may be configured to change the level of ionization based on the detection of the physiological characteristic. In some cases, the physiological characteristic may be detected sleep. Optionally, the controller may be configured to adjust the level of ionization based on the detection of a sleep state. For example, the level of ionization may be reduced upon detection of a deep sleep state or rapid eye movement (REM) sleep state. A deep sleep state or slow wave sleep state is also known as non-rapid eye movement (Non-REM) sleep stages 3 and 4 which form the deeper part of the sleep cycle wherein the brain emits delta wave activity. The physiological characteristic may include a detected respiratory event. The detected respiratory event may be a detected inspiratory cycle.

Optionally, in some cases, the controller may be further configured to turn on and turn off the ionizer while continuing to control the flow generator to generate the flow of breathable gas. The apparatus may further include a filter to attract charged contaminants from the ionized flow of breathable gas. The filter may be an electret filter.

Optionally, the ionizer may be located proximate to the flow generator. The apparatus may further include a secondary ionizer. The secondary ionizer may be located proximate to the patient interface. Such a dual stage or multi-stage ionization configuration may beneficially allow the initial ionizer(s) to promote cleaning of the breathable gas and secondary ionizer(s) to promote inhalation of ionized gas. Optionally, the apparatus may also include a humidifier. The humidifier may have a gas flow input in gas flow communication to a gas flow output of the ionizer.

In some cases, the ionizer may be formed by an array of ion generators. The controller may be configured to selectively activate different portions of the array. In some cases, the processor may be configured to control the flow generator to programmatically set the flow of breathable gas at the pressure above atmospheric pressure. The controller may control the flow of breathable gas to maintain a target ventilation. Optionally, the controller may control the flow of breathable gas to set the pressure above atmospheric pressure to alleviate events of sleep disordered breathing.

In some cases, the apparatus may include an ion sensor to generate a signal indicative of a level of ionization of the ionized gas. The controller may also be configured to control the ionizer to change the level of ionization based on a measure of ionization from the ion sensor.

Optionally, the apparatus may include a delivery conduit to couple between the flow generator and patient respiratory interface. The delivery conduit may have a material with a charge state to repel the ionized breathable gas. Such a repulsion force may be at or along the walls or flow surface of the air delivery conduit to prevent or reduce the ionized gas from sticking or attaching therein and thereby may reduce resistance of the air delivery tube. This may also be considered a shear on the flow path boundary that reduces resistance. In some cases, the delivery conduit may include one or more charge elements to set a charge state of the delivery conduit (e.g., its flow surface) to repel the ionized breathable gas.

Some cases of the present technology may include a control method of a respiratory treatment apparatus for generating a controlled supply of ionized breathable gas. The control method may include generating with a flow generator a flow of breathable gas at a pressure above atmospheric pressure. The control method may further include ionizing with an ionizer the flow of breathable gas at a level of ionization. The control method may further include controlling, with a processor, a change to the level of ionization of the flow of breathable gas to set the ionization to a plurality of different ionization levels. In some cases of the control methodology, the change to the level of ionization may be a decrease of the level of ionization over a period of time. In some cases of the control methodology, the change to the level of ionization may be an increase of the level of ionization over a period of time. In still further cases of the control methodology, the change to the level of ionization may include pulsing of the level of ionization over a period of time.

Optionally, the change to the level of ionization of the methodology may include a decrease of the level of ionization after expiration of a wake period.

In some cases, the control methodology may further include detecting with a sensor a physiological characteristic. In such a case, the change to the level of ionization may be based on the detection of the physiological characteristic such as detected sleep and/or a detected respiratory event such as a detected inspiratory cycle. In some such cases, the change to the level of ionization may include adjusting the level of ionization based on the detection of a sleep state. For example, the level of ionization may be reduced upon detection of a deep sleep state and/or REM sleep state.

In some cases, the control method may further include turning on and turning off the ionizer while continuing to control the flow generator to generate the flow of breathable gas. Additionally, the method may further include filtering the ionized flow of breathable gas to attract charged contaminants from the ionized flow of breathable gas, such as with an electret filter. In some cases, the ionizing may be performed proximate to the flow generator and secondary ionizing may be performed proximate to a patient interface. The method may further include humidifying the ionized breathable gas.

In some such methods, the ionizer may include an array of ion generators and the method may involve selectively activating different portions of the array. In any such cases, the processor may control the flow generator to programmatically set the flow of breathable gas at the pressure above atmospheric pressure. The processor may control the flow of breathable gas to maintain a target ventilation. The processor may control the flow of breathable gas to set the pressure above atmospheric pressure to alleviate events of sleep disordered breathing.

In some cases, the control method may involve generating a signal indicative of a level of ionization of the ionized gas with an ion sensor. The controlling, with the processor, may then set the ionizer to change the level of ionization bated on a measure of ionization from the ion sensor.

In some cases, the method may involve repelling the ionized breathable gas with a delivery conduit. In some such cases, the delivery conduit may be adapted to couple between the flow generator and a patient respiratory interface and may have a material with a charge state to repel the ionized breathable gas. The material may be provided along a flow surface or internal wall of the delivery conduit. Optionally, the method may also involve charging with a charging element the delivery conduit such that the charging element sets a charge state of the delivery conduit to repel the ionized breathable gas.

Some examples of the present technology may include a solid state flow generator such as for a respiratory apparatus for generating a controlled supply of breathable gas. The flow generator may include a set of ionizers configured to propel a flow of breathable gas, the set of ionizers configured with a flow path adapted to couple with a user respiratory interface. The flow generator may also include a controller coupled with the set of ionizers. The controller may be configured to selectively activate the ionizers for propelling the flow of breathable gas.

Optionally, the set of ionizers for such a flow generator may be arranged in a serial configuration in the flow path. Moreover, the controller may then be configured to selectively activate an increasing number of the ionizers to increase propulsion of the flow of breathable gas. In some cases, the set of ionizers may be formed as an ionizer sheet or in a grid configuration. Optionally, the flow path of the ionizer of such flow generators may be helical and the set of ionizers may be arranged along the helical flow path.

In some cases, the ionizer flow generator may include a sensor and the controller may be configured to activate a sub-set of the set of ionizers based on a signal generated from the sensor. For example, the sensor may be a flow sensor, and the controller may be configured to selectively activate a sub-set of the set of ionizers based on a measure of flow from a signal from the flow sensor. By way of further example, the sensor may be a pressure sensor, and the controller may be configured to selectively activate a sub-set of the set of ionizers based on a measure of pressure from a signal of the pressure sensor.

Optionally, in some cases, the flow generator may include a neutralizer. The neutralizer may be configured to deionize the propelled flow of breathable gas of the flow path of the flow generator.

Optionally, the set of ionizers may include a plurality of carbon fiber brush ion generators. Still further, the set of ionizers may optionally include a plurality of honeycomb cell ion generators.

In some cases, such flow generator(s) may have a flow path with a divider. The divider may separate two or more channels and each channel may include a set of ionizers. The channels may include an inspiratory channel and an expiratory channel. The divider may be arranged helically in a cylindrical delivery tube. The divider may be configured as a ground element. The divider may be configured for removably coupling within a delivery conduit.

Additional features of the technology will also be apparent from consideration of the information contained in the following detailed description, drawings, abstract and claims.

Any of the aspects and features of the described example embodiments may be combined with aspects of other examples to realize yet further embodiments.

BRIEF DESCRIPTION OF THE DRAWINGS

The present technology is illustrated by way of example, and not by way of limitation, in the figures of the accompanying drawings, in which like reference numerals refer to similar elements including:

FIGS. 9a and 9b are illustrations of a flow generator implemented with carbon brush ionizers;

FIG. 10 is an illustration of a flow generator with honeycomb shaped ionizer elements;

FIGS. 13a and 14a are front views of first and second flow structures respectively for an example helical generator having integrated ionizers;

FIGS. 13b and 14b are top plan views of the flow structures of FIGS. 13a and 14a respectively.

DETAILED DESCRIPTION

The present technology involves methods and devices for respiratory ionization therapy, such as a provision of negatively charged air. Hemoglobin is the iron-containing oxygen-transport metalloprotein in the red blood cells. Hemoglobin iron is basically a cation and thus, positively charged. Providing ionized air to a user or patient that includes a negatively charged oxygen component may permit improved blood absorption of oxygen given the positively charged hemoglobin oxygen-transport mechanism of the blood. In some cases, this improved oxygen affinity may result in reduced need for a secondary source of supplemental oxygen. Such therapy may also help to disinfect bacteria and viruses in breathable air or in the patient's lungs and may reduce degradation or inflammation of lung tissue or lung condition. Receiving ionized air may also aid sleep onset. However, it may not be desirable to provide too high a level of ionization for extended periods of time. Accordingly, some apparatus of the present technology may provide a controlled delivery of ionized air so as to set different levels of ionization during suitable times in a treatment, regime. Such treatment may be suitable for patients with respiratory insufficiency (RI) such as chronic obstructive pulmonary disease (COPD). However, such therapy may also be suitable for other users or respiratory issues, such as for example, sleep disordered breathing, sleep apnea, or other respiratory treatment that may involve a breathable supply of gas.

Figure 1:
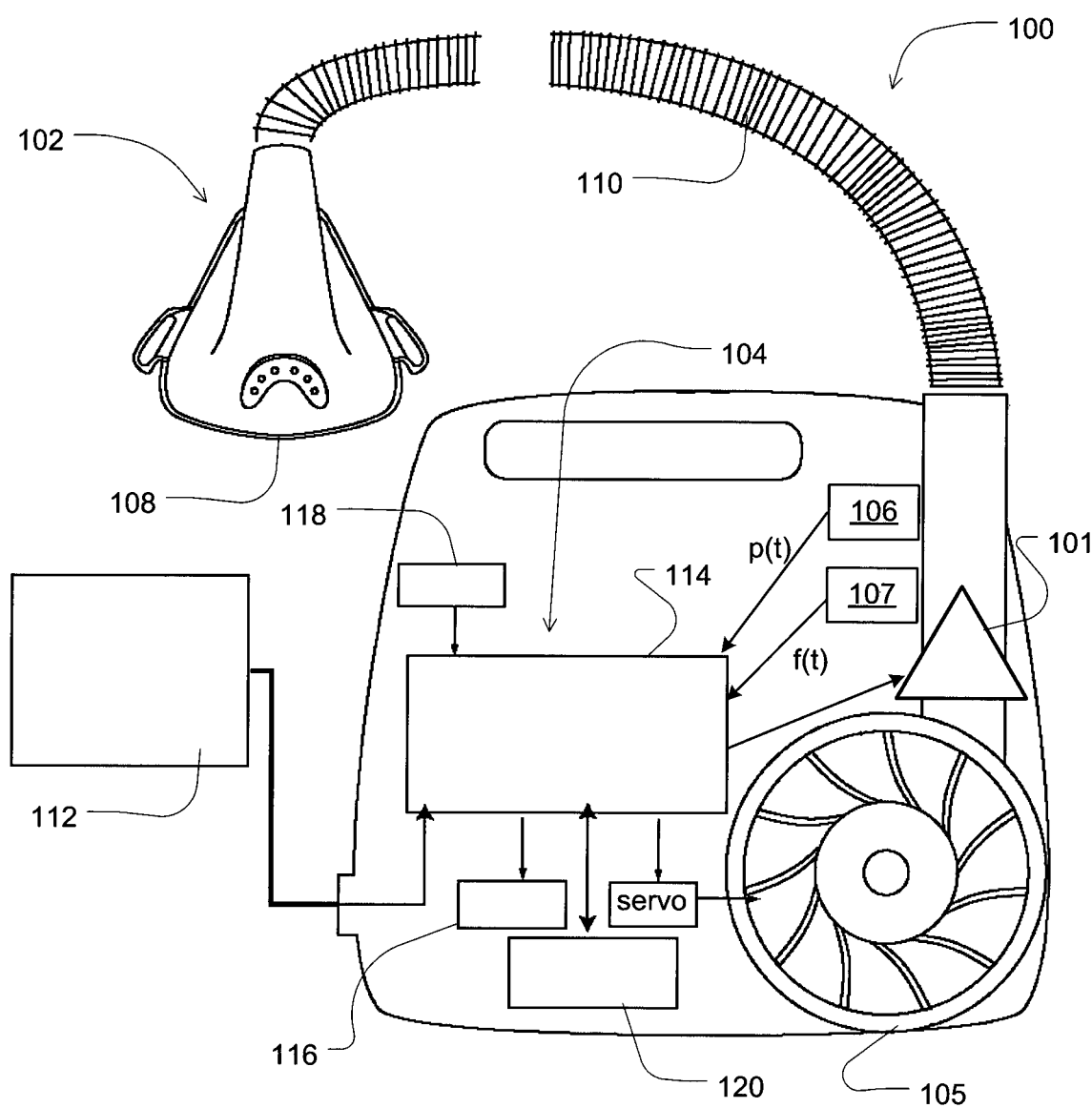
FIG. 1 illustrates example components of an ionization therapy device for a controlled generation of a respiratory ionization therapy.

An example embodiment of a device for implementing a respiratory ionization therapy of the present technology is illustrated in FIG. 1. In the embodiment, the ionization therapy device 100 produces a breathable gas (e.g., air) with ions, such as anions. The ionization therapy device 100 will typically include a patient respiratory interface 102, a delivery tube 110, a controller 104, an ionizer 101, and a flow generator such as a servo-controlled blower 105.

The patient respiratory interface, such as a mask 108 as shown together with the delivery tube 110, provides a respiratory treatment to the patient's respiratory system via the patient's mouth and/or the patient's nares. Optionally, the patient respiratory interface may be implemented with a nasal mask, nose & mouth mask, full-face mask, nasal pillows, nasal cannula or tracheostomy tube.

With the flow generator, the ionization therapy device 100 can also be configured to generate a respiratory flow or pressure treatment toward or in the patient respiratory interface. The nature of such flow or pressure treatments may vary depending on the type of user or patient treated. Example pressure/flow treatment will be described in more detail herein but may be any suitable respiratory treatment therapy.

The ionization therapy device 100 may also typically include an ionizer 101. The ionizer may be located in the flow path of the ionization therapy device 100 that generates flow toward or pressure in the patient respiratory interface. In the case of implementation within the flow generator, the ionizer may either be upstream or downstream of the blower. As illustrated in the example of FIG. 1, the ionizer is downstream of the blower. In the example, the ionizer is integrated with the flow path of the flow generator. However, the ionizer may also be implemented as an add-on component or module such as one that removably couples between the delivery tube 110 and the flow generator housing. In such a case, the module may include a controller and/or be in electrical communication, such as on a communications bus, with a controller of the flow generator. Optionally, such an add-on may couple to an inlet of the blower 105. Other structural configurations may also be implemented such as the configuration discussed in more detail herein with reference to FIG. 5.

The ionizer 101 will typically be configured to ionize the breathable gas produced by the flow generator. The ionizer may include electrostatically charged elements to produce either positively or negatively charged gas ions in the pressurized air produced by the blower. In the case of the anion generator, the electrostatically charged elements produce the negatively charged gas ions. In some examples, the ionizer may be an ionization generator such as a carbon fiber brush multiple ion corona discharge. However, other types of ionizers may also be implemented. One such example of a negative ion generator is the ionizer or means for generating negative ions as described in U.S. Pat. No. 4,102,654, the disclosure of which is incorporated herein by reference.

The controller 104 or processor 114 will typically be coupled, electrically, with the ionizer 101. In some cases, the ionizer 101 may be controlled by the controller, such as with a suitable activation circuit, to selectively increase or decrease the electrostatic charge, voltage and/or current supplied to, or to otherwise gate, the operation of the production elements (e.g., electrodes, anodes and/or diodes) of the ionizer so as to increase or decrease the level of ionization. Optionally, it may be controlled by powering the ionizer 101, wholly or in part, on or off at suitable times. For example, in some cases, the ionizer may be formed by an array of production elements (e.g., a set of electrodes or electrode tube segments (cathodes and/or anodes) etc. in a honeycomb array through which or by which air to be ionized will pass) which may each be selectively operated by the controller to increase or decrease the level of ionization produced by the ionizer. In some such cases, a greater number of activated production elements of the array may generate a higher level of ionization and a relatively fewer number of activated production elements of the array may generate a lower level of ionization.

Typically, the controller's programmatic operation of the ionizer will be independent from the controller's programmatic operation of a pressure/flow of a respiratory gas treatment from the blower, when implemented. In other words, the controller may continue to provide the pressurized flow of breathable gas treatment with the blower to a patient or user whether or not the ionizer, in whole or in part, is activated or deactivated by a controller to ionize the breathable gas. Thus, the controller may independently make changes to the settings for generating the pressure or flow of gas and to the settings for ionization. However, typically, when the ionizer is ionizing the gas, the controller will control the blower to generate the pressure/flow of gas.

Accordingly, the controller 104 (such as one including a processor 114 or processors) may be configured to implement particular programmatic control methodologies such as the flow/pressure gas treatment control algorithms and/or the ionization control algorithms described in more detail herein. Thus, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. With such a controller or processor, in addition to methodologies for pressure and/or flow control, the ionization therapy device can be used for setting different ionization levels, setting or changing the ionization levels at certain times and/or setting or changing ionization levels in response to detected conditions. Thus, the processor may control the level of ionization, for example, as described in the embodiments discussed in more detail herein with reference to FIGS. 2, 3 and 4.

In some cases, the ionization therapy device 100 may also optionally be equipped with one or more sensors. For example, it may optionally include a flow sensor 107 and/or a pressure sensor 106, which may be coupled with the patient respiratory interface. The flow sensor may generate a signal representative of the patient's respiratory flow. The signals from the sensors may be processed to detect obstructive or central apneas, hypopneas, hypoventilation, hyperventilation, cardiogenic airflow, respiratory rates, respiratory cycles, respiratory phase (e.g., inspiration and/or expiration) and other respiratory related parameters from the signals measured by the sensors. In some embodiments, flow proximate to the mask or delivery tube 110 may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure. The pressure sensor 106 may be a pressure transducer. Although the pressure or flow sensors are illustrated in a housing of the controller 104, they may optionally be located closer to the patient, such as in the mask or delivery tube 110. Other devices for generating a respiratory flow signal or pressure signal may also be implemented. For example, a motor RPM sensor may be utilized to estimate pressure or flow information supplied by the flow generator device based upon the characteristics of the system. One such example is the device described in U.S. patent application Ser. No. 12/294,975, filed Oct. 30, 2008 and PCT/AU05/01688, the entire disclosures of which are incorporated herein by reference.

In some cases, an ionization device 100 of the present technology may include one or more ion sensors such as an ion, meter, anion sensor etc. The sensors may be located for example, proximate to the patient interface (e.g., in or at the mask) and/or proximate to each ion generator. The controller may detect or measure the level of ions or anions in the breathable gas generated based on a signal from one or more of such sensor(s). In some cases, the controller may increase or decrease ion generation by control of the ion generator(s) based on a signal from the sensor(s) that may be indicative of the level of ionization. For example, it may control ionization so that the measure is servo-controlled to satisfy a desired or set target level of ionization. Thus, the control of the ion generator(s) may optionally be by closed loop control.

Optionally, the ionization therapy device 100 may also include additional diagnosis sensors 112 that may assist in the setting of treatment of the present technology. For example, the device may include an oximeter. The oximeter may generate a signal representative of a blood oxygen level of a patient. A suitable example oximeter or monitor device may optionally be any of the devices disclosed in International Patent Application No. International Application No. PCT/AU2005/001543 (Pub. No. WO/2006/037184) or International Patent Application No. PCT/AU1996/000218 (Pub. No. WO/1996/032055), the disclosures of which are incorporated herein by cross-reference. As disclosed in these incorporated PCT applications, the monitor may serve as diagnosis sensors that can also optionally provide a blood pressure and/or heart or pulse rate monitor for measuring a heart rate and/or blood pressure of the patient.

For example, the sensors may be configured to provide an indication of the resistance of the lungs. A measure of the resistance of the lungs may provide an indication of a reduction or increase in inflammation of the lungs indicating a level of patient improvement or worsening. As a result of the indication of the level of patient improvement or worsening adjustments in the therapy may be made by the controller.

In some embodiments, the diagnosis sensors may also include an electrocardiography (ECG) monitor. Such a device may be configured to detect cardiac-related characteristics such as a heart rate and may also determine respiratory events (such as central or obstructive apneas, hypopneas, etc.) Optionally, these parameters may be determined by the analysis algorithms of controller 104 based on transmission of the ECG data to the controller or they may be determined by the monitor and be transmitted to the controller 104.

In some cases, ionization treatment device may include sensors for detecting sleep such as Electroencephalography (EEG) sensors. It may include a sleep monitoring system such as that of BiancaMed Limited described in U.S. Patent Application Publication No. 2009/0131803, published on May 21, 2009, the entire disclosure of which is incorporated herein by reference. This BiancaMed Limited system is a sleep monitoring system that includes an ECG device and a respiration inductance plethysmogram which monitor cardiac activity and physical (ribcage) respiration respectively. The ionization treatment device may also include contact and non-contact biomedical sensors such as any of the sensors described in United States Patent Application Publication No. 2009-0203972, filed Nov. 26, 2008, the entire disclosure of which is incorporated herein by reference. Such a non-contact monitoring sensor may transmit and then process reflected radio frequency signals received, such as ultrawideband radio-frequency signals, so as to detect bodily movement, respiration and/or cardiac activities for assessment of sleep and sleep transitions (e.g., asleep or awake detection) as well as respiratory events (e.g., apnea, central apnea, obstructive apnea, hypopnea, etc.).

In some embodiments, the diagnosis sensors may include other movement sensors. For example, a suprasternal notch sensor or chest band may be implemented to generate a movement signal that is indicative of patient effort during respiration. Other suitable sensors may include the movement sensing devices disclosed in International Patent Application No. PCT/AU1998/000358 (Pub. No. W01998/052467), the disclosure of which is incorporated herein by cross-reference. The movement sensors thus may provide a measure of patient effort and/or respiration rate and may be used as an alternative to a flow sensor or in conjunction with other sensors in the determination of physiological characteristics.

Based on sensor signals, such as flow f(t) and/or pressure p(t) signals, the controller 104 with one or more processors 114 may, in addition to ionization control signals, also generate blower control signals. For example, the controller may generate a desired pressure set point and servo-control the blower to meet the set point by comparing the set point with the measured condition of the pressure sensor. Thus, the controller 104 may make controlled changes to the pressure delivered to the patient interface by the blower 105. Optionally, such changes to pressure may be implemented by controlling an exhaust with a mechanical release valve (not shown) to increase or decrease the exhaust while maintaining a relatively constant blower speed.

With such a controller or processor, the apparatus can be used for many different pressure treatment therapies, such as the pressure treatments for sleep disordered breathing, Cheyne-Stokes Respiration, obstructive sleep apnea (e.g., CPAP (continuous positive airway pressure), APAP (automatic positive airway pressure), Bi-Level CPAP, CPAP with expiratory pressure relief), nasal high flow air therapy (HFAT) etc., or combinations thereof by adjusting a suitable pressure or flow delivery equation. In some examples, an automated pressure adjustment therapy for sleep disordered breathing may be delivered by the methodologies described in U.S. Patent Application Publication No. US-2011-0203588-A1, published on Aug. 25, 2011, the entire disclosure of which is incorporated by reference. By way of further example, the pressure treatment therapies of the devices described in U.S. Pat. Nos. 6,532,957, 6845,773 and 6,951,217, which are incorporated herein by reference in their entireties, may be implemented with the ionization therapy device 100 of the present technology. For example, as described in these patents, the controller and flow generator may be configured to ensure delivery of a specified or substantially specified target ventilation, for example, a minute ventilation, a gross alveolar ventilation or an alveolar ventilation, to the patient interface during the course of a treatment session by comparing an measure of ventilation with the target ventilation; or delivery of a tidal volume by comparing a measure of tidal volume with a target tidal volume. This may be accomplished with pressure variations that provide a bilevel form of therapy or some other form of therapy that may more smoothly replicate changes in a patient's respiration cycle.

Accordingly, the signals from the sensors may be sent to the controller 104. Optional analog-to-digital (A/D) converters/samplers (not shown separately) may be utilized in the event that supplied signals from the sensors are not in digital form and the controller is a digital controller. Based on the signals from the sensor(s), the controller assesses the changing condition of the patient or user in controlling the settings of the device.

The controller may optionally include a display device 116 such as one or more warning lights (e.g., one or more light emitting diodes). The display device may also be implemented as a display screen such as an LCD. Activation of the display device 116 will typically be controlled by the controller. The display device may be implemented to visually show information to a user of the ionization therapy device 100 or a clinician or physician, such as historic profiles of time verses ionization level graphs from one or more treatment sessions, or manual settings to be entered as data to the controller for setting such profiles. The display device 116 may also show a graphic user interface for operation of the device. User, clinician or physician control of the operation of the ionization therapy device 100 may be based on operation of input switches 118 that may be sensed by the controller or processor.

Optionally, the controller may also include a communications device 120 for receiving and/or transmitting data with ionization therapy device 100. For example, the communications device may be a wireless transceiver such as Bluetooth or WIFI transceiver. The communications device may also be a network, communications device such as a phone modem and/or network card and may be implemented to send messages via the internet directly or through a computer to which the detection device may be docked. In general, the communications device 120 may be used to transmit messages or data to other clinician or physician assessable apparatus such as a multi-patient monitoring system that allows a physician to review data from the ionization therapy device 100 serving as a remote patient data recording devices. In these systems, a database may be provided to record historic ionization data, such as the profiles provided and the levels of ionization provided over time with the device. Such data may be provided in association with data representing timing of other detected physiological characteristics (e.g., respiratory events or sleep state) as described in more detail herein. Physicians or clinicians may receive a report with such use and event data recorded by ionization therapy device 100.

Figure 2:
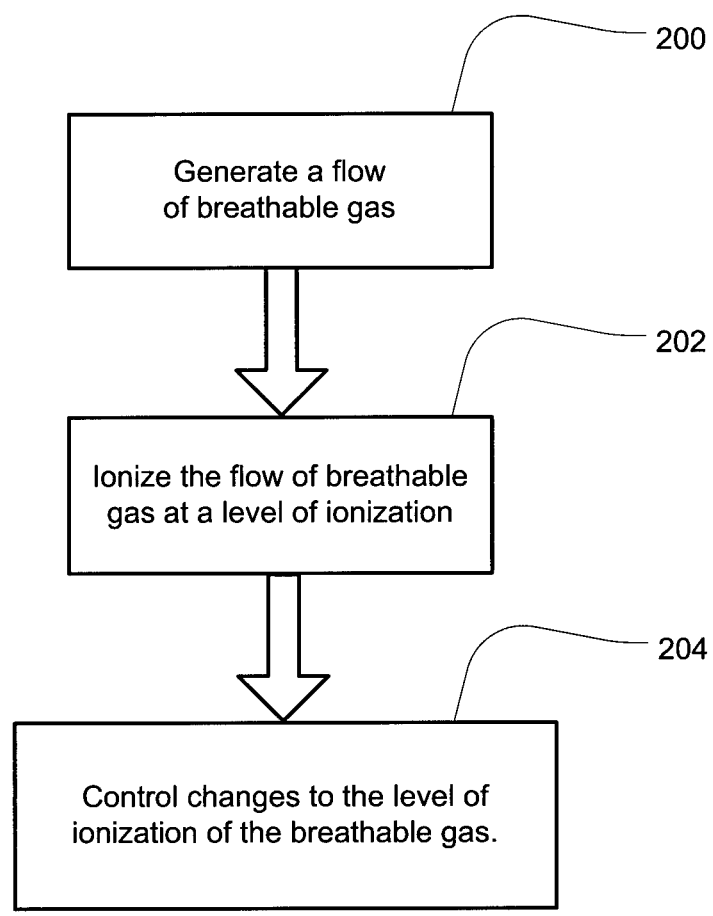
FIG. 2 is an example methodology for a device that implements a controlled respiratory ionization therapy.

One example methodology or algorithm of the controller 104, or one or more processors, of the ionization therapy device 100 is illustrated in the flow chart of FIG. 2. In process 200, the ionization therapy device 100 may generate a pressurized flow of breathable gas. The pressurized flow of breathable gas may also be directed to a patient interface for delivery to a patient. As previously mentioned, the processor may servo-control the flow generator to deliver a pressure support treatment that satisfies a target ventilation, for example. Optionally, such a treatment may encompass a positive airway pressure treatment (e.g., a CPAP or bi-level) to treat upper airway issues so as to treat sleep disordered breathing.

During at least some portion or portions of such a flow or pressure treatment control process, in process 202, the ionization therapy device 100 will ionize the flow of breathable gas to a set level of ionization. For example, based on one or more signals from the controller 104, the ionizer 101 will produce negatively charged gas ions within the pressurized flow of breathable gas produced by the blower, thus producing an ionized flow of breathable gas.

Based on the control algorithms implemented in the controller 104, the ionization therapy device will then control changes to the level of ionization of the breathable gas in process 204. For example, the controller may be configured to adjust the level of ionization so as to promote sleep. In one such example, the controller may implement a therapy session (e.g., a sleep period or night of use with the device) so as to provide a level of ionization during the beginning of the therapy session or while the user or patient is likely to be awake but change the ionization production level thereafter (e.g., increase, reduce or cease) when the user or patient is likely to be asleep. Such a control methodology may be programmatically implemented in various ways.

In one example, the controller may implement a timed wake period, such as with a timer or countdown timer or other event detection, that begins with the start of the pressure or flow treatment process of the ionization therapy device 100. Optionally, such a timed wake period may begin with activation of a user interface control (e.g., an ionization start button) by a user desiring to go to sleep or back to sleep. Still further, it may begin as a function of detected events such as events detectable from one or more signals of one or more sensors of the ionization therapy device 100, such as an intelligent start feature. In such a case, the controller of the treatment apparatus may be configured to detect a pressure or flow change at the patient interface by analysis (e.g., comparison of a measure from a signal with a threshold) of a signal from a pressure or flow sensor so as to detect when a patient initially breaths into the patient interface after putting it on their face. Upon such a detection, the controller may activate the ionizer to begin ionization at a pre-set level.

During the timed wake period, the ionization level may be delivered at a first level, e.g., an initially high level. For example, the ionizer may be controlled such that all production elements are operating and producing at full capacity. When the timed wake period ends, the controller may then adjust a setting of the ionization level. For example, when a pre-set time of the timed wake period lapses (e.g., a timer of the controller reaches a pre-set threshold or a countdown timer reaches zero), the controller may then automatically change the ionization level (e.g., reduce the ionization level to a second different level or automatically discontinue the ionization level or begin an oscillation of ionization levels). For example, the controller may deactivate a subset of the production elements of the ionizer while leaving others active and/or may reduce a voltage level of some or all of the production elements such that fewer ions are produced.

The duration (e.g., the amount of time) of the timed wake period and/or the ionization settings (e.g., the first level (e.g., 100% production) during the timed wake period and second level (e.g., 25% production) after the timed wake period) may be pre-set by a clinician or physician. Typically, the duration of the timed wake period may be a time during which it takes a patient or user to fall asleep once the use of the device is initiated. In some such cases, the duration may be a time in the range of approximately 30 minutes to 60 minutes, or some other suitable time.

In some cases, the end of or the duration of the timed wake period may be a function of detected events such as events detectable by the controller from one or more signals of one or more sensors of the ionization therapy device 100. For example, the end of the timed wake period may be based on a detection of one or more patient respiratory cycles. For example, the duration may be a respiratory cycle count determined by signal analysis of a signal from a sensor. In some such cases, by analysis of a signal from a flow or pressure sensor, the controller may detect patient or user inspiration (e.g., any known cycle detection methodology). A number of such detected inspiratory cycle events may be counted beginning with the start of the timed wake period. When the counted number reaches a pre-set threshold number, the controller may then end the timed wake period and adjust the setting of the ionization level generated by the ionizer (e.g., increase, oscillate, reduce or stop). In some such cases, the duration may be a count in the range of approximately 360 cycles to 720 cycles, or some other suitable cycle count.

In some cases, the detected end of the timed wake period may be another analysis of respiration. For example, by analysis of a signal from a sensor, such as a flow sensor, effort sensor or other non-contact sensor, the controller may determine a respiratory rate. When the respiratory rate falls below a pre-set threshold rate, such as one indicative of sleep, and, optionally, stays below that rate for a pre-set period of time (e.g., approximately 5 to 10 minutes), the timed wake up period may be ended by the controller and the controller may then change the setting of the ionizer (e.g., lower or cease the level of ionization). In some cases, the threshold respiratory rate may be automatically determined. For example, the controller may determine an average respiratory rate during an initial period of use (e.g., approximately 2-5 minutes) of the device, which may then be taken as the threshold rate for the change in ionization.

In some examples, the timed wake period may be established based on a detection of a sleep state by the controller. For example, any known method for sleep detection, arousal detection or sleep state detection may be employed with any sensors coupled with the controller of the device. Such detection methodologies may include, for example, the detection methodologies described in United States Patent Application Publication No. 2009-0203972, filed Nov. 26, 2008, the entire disclosure of which is incorporated herein by reference. Additional examples of such detection methodologies are described in U.S. patent application Ser. No. 13/383,341, filed on Jan. 10, 2012, the entire disclosure of which is incorporated herein by reference. In some such examples, the timed wake period may be initiated or re-initiated upon detection of arousal from sleep or an awake sleep state. Similarly, the timed wake period may end upon detection of a sleep state (e.g., REM or a stage of non-REM sleep) by the controller. For example the level of ionization may be reduced or ended upon detection of a deep sleep state, such as stage 3 or 4 Non-REM sleep, and/or upon detection of REM sleep. The level of ionization may be increased or recommenced upon detection of an awake state and/or a light sleep stage, such as stage 1 Non-REM sleep state and/or a stage 2 Non-REM sleep.

In some cases, the provision of ionized gas may be controlled in accordance with additional detected physiological events or conditions. For example, in response to an analysis of a signal from an oximeter, the controller may activate or deactivate the ionizer or raise or lower the level of ionization during control of a pressure/flow respiratory treatment. In some such cases, an analysis of a blood oxygen level, such as based on a comparison of a threshold, may serve as a trigger to the controller to change the set level of ionization provided by the ionizer. For example, if the blood oxygen level falls below a threshold, the controller may initiate or increase the set level of ionization. Such an ionization level may be delivered for a pre-set period of time. By way of further example, if the blood oxygen level rises above a threshold the controller may terminate or decrease the set level of ionization provided by the ionizer. Such a test may also serve to terminate any of the periods of ionization treatment described herein.

Similarly, the controller may be configured to detect events of sleep disordered breathing (SDB) including, for example, apnea, hypopnea and/or hypoventilation, such as by an analysis of a signal from a flow sensor. Examples of such detection methodologies are disclosed in U.S. patent application Ser. No. 12/781,070, filed on May 17, 2010 and PCT Patent Application No. PCT/AU2012/000270, filed on Mar. 15, 2012, the entire disclosures of which are incorporated herein by reference. In response thereto, or in response to detection of a pre-set number of such events of SDB, the controller may similarly control an increase in the level of ionization, or start ionization, for a period of time.

In some cases, an analysis of a signal from the flow and/or pressure sensor may serve to deactivate operation of the ionizer. For example, by comparing a pressure signal with a threshold, it may be determined that a low pressure condition exists such that the patient interface or mask is no longer being worn by the user or patient. In such a detected case, the controller may deactivate the ionizer. Similarly, if the controller no longer detects a patient respiratory cycle after a period of time, such as from an analysis of a flow signal from a flow sensor, the controller may similarly deactivate the ionizer.

To ensure a limited operation of the ionizer, in some examples, the controller may additionally enforce a safety maximum use limit that may override the controlled timed wake period or other controlled activation of the ionizer. For example, while the ionizer may be controlled to provide an ionized gas treatment at certain levels and do so in accordance with detected events from an analysis of signals from one or more sensors or initiation by a user activated button, the controller may further monitor the time of operation and/or the levels of operation of the ionizer. If the ionizer exceeds any pre-set maximum safety time limit of operation or pre-set maximum time at certain levels of ionization during some treatment period (e.g., one nights use) with the device, the controller may automatically shut down the ionizer and automatically prevent any further or continued operation of the ionizer until a pre-set shut down time limit has passed (e.g., a period of 12 hours has lapsed, etc.). In the event of such a shutdown by the controller, the controller of the flow generator may nevertheless continue operation so as to continue to control the blower to provide a flow or pressure respiratory treatment to a patient or user but doing so without permitting the ionization of the breathable gas by the ionizer.

Figure 3:
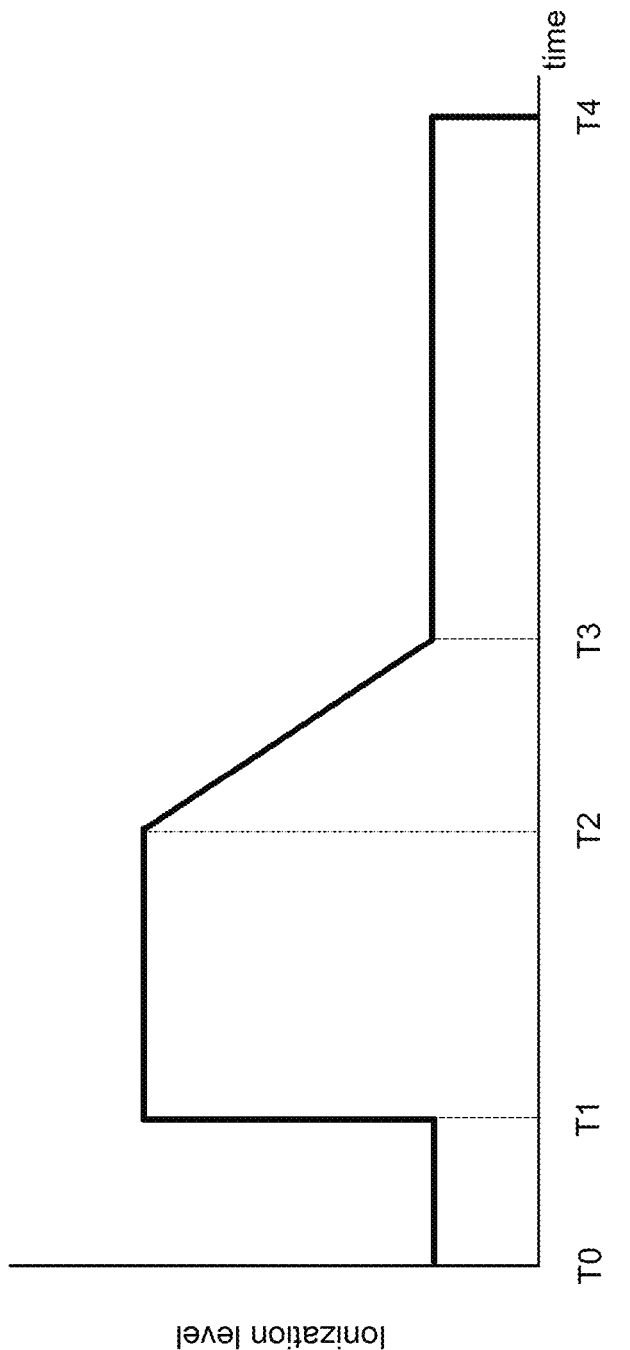
FIG. 3 is an example graph illustrating controlled changes made to ionization levels by a controller of an example respiratory ionization therapy apparatus of the present technology.

A signal graph illustrating an example controlled operation of the ionizer of an ionization therapy device 100 is illustrated in FIG. 3. At time T0, an operation of the ionization therapy device 100 may begin, such as the device producing a pressurized breathable gas from the blower and/or detecting conditions with one or more sensors. During this time, the ionizer 101 may be deactivated by the controller or, as illustrated, the ionizer may be activated at an initial low level. At time T1, the controller may increase (or initiate) ionization such as by increasing the ionization level. This may correspond to the start of a timed wake period or other detected condition as previously discussed for initiating or increasing ionization. The controller may then continue to control the ionizer to operate at an ionization level (e.g., a maximum level) until time T2. Time T2 may correspond to an end of the timed wake period or another detected condition as previously discussed for reducing the ionization level. At this time, the controller may gradually change the ionization level, such as by ramping down the ionization level to a lower level at time T3, the lower ionization level at time T3 may or may not be the same as the ionization level provided during time T0. The controller may then continue to operate the ionizer at the lower level until time T4, which may correspond with an end of a treatment session with the device, such as the end of the night, or the controller determining that the safety maximum use limit has been reached. Although a smooth ramping of the ionization level is illustrated between times T1 and T2, and a single step is illustrated between times T0 and T1, the controller may optionally be configured to control each of these changes to the ionization levels, as well as other such changes described herein, in a plurality of steps. Also the change from times T0 to T1 may include a ramping up to a predetermined level of ionization rather than a single step increase to the time T1 level of ionization as indicated in FIG. 3.

Figure 4:
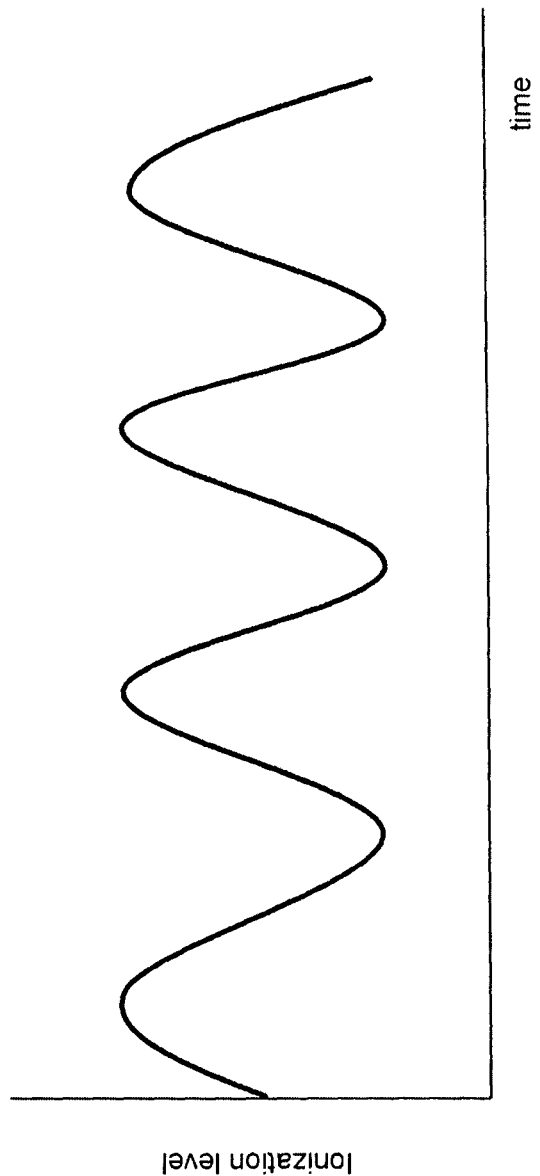
FIG. 4 is an another example graph illustrating controlled changes made to ionization levels by a controller of an example respiratory ionization therapy apparatus of the present technology.

A further signal graph illustrating another example controlled operation of the ionizer is illustrated in FIG. 4. The graph illustrates a controlled oscillation of the level of ionization by the controller. In this example, sinusoidal pulses of the ionization level may be controlled. However, other variations of the ionization levels may be implemented, e.g., square wave pulses, etc. In such cases, the ionization oscillation may vary between a higher ionization level and a lower ionization level. As a result, the controller may vary the levels over a time period, such as a night's treatment session. Alternatively, the oscillation may vary between an ionization level at the pulse peak and no ionization (e.g., ion generator off) at the pulse trough. Such pulses may be initiated upon completion of the timed wake period. The period for each wave may be set based on any desired timing for pulsing the ionization level. In some cases, the pulses may be generated synchronously with detected respiration. For example, the level of ionization may increase during inspiration (e.g. to a first ionization level) and decrease during expiration (e.g., to a second ionization level or alternatively, may be turned off so as to provide no ionization level during expiration. In such cases, the controller may detect inspiration by analysis of a signal from a flow sensor and trigger the increase in level of ionization in response thereto and may detect expiration by analysis of the signal and decrease the level of ionization in response thereto. In still further cases, the pulses may be out-of-synch with patient respiration. For example, a pulse may extend over several breathing cycles (e.g., a peak ionization level that extends longer than a single breathing cycle or two or more cycles).

Figure 5:
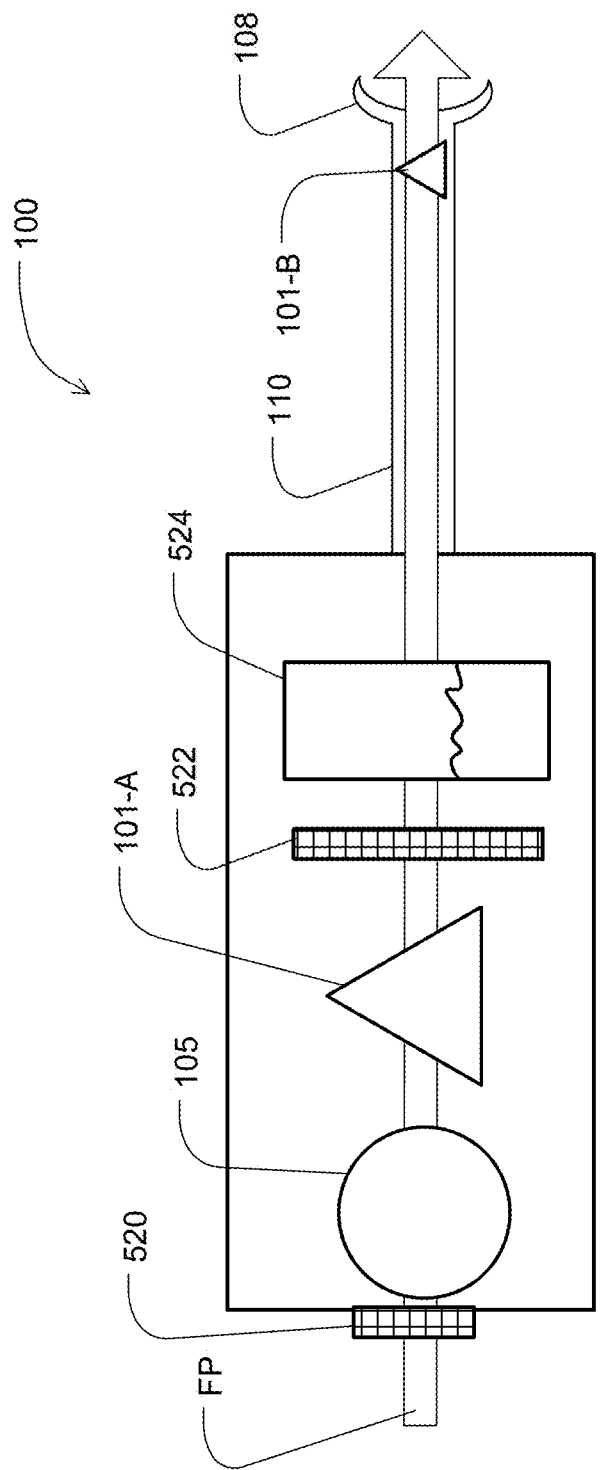
FIG. 5 is a diagram illustrating a further example ionization therapy device suitable for use in some embodiments of the present technology.

In some configurations, the ionization therapy device 100 may be implemented with multiple ionizers 101 located in different portions of the breathable gas flow path FP of the device. The ionization therapy device 100 may include an array of ion generators for example 2, 3, 4 or more ion generators that may be controlled to ionize the flow of breathable gas at the same time or separately according to different profiles. One such example is illustrated in FIG. 5. The figure illustrates symbolically the flow path (FP) of the ionization therapy device 100. In this regard, ionization therapy device 100 may have components similar to that of the device illustrated in FIG. 1. Ambient air may be drawn in by the servo-controlled blower 105 through an inlet that may include an optional filter 520, such as a particulate air filter or High-Efficiency Particulate Air (HEPA) filter, to remove particles from the air so as to clean the air. The blower 105 may then expel pressurized air into the path of a first ionizer 101-A that is also controlled by a controller (not shown). The ionized air may then pass through or across a ground element 522, such as a grounded filter or electret filter. Any remaining pollutants or contaminants in the air that are charged by the ionizer 101-A may then be captured by the ground element 522 so as to purify the air and thereby prevent charged contaminants from entering the user or patient's respiratory system. In some cases, the charging by the ionizer destroys light bodies, such as bacteria or viruses, which are then captured by the ground element filter (e.g., anode or cathode). The ground element may be an array, grid or mesh filter that may be removable for maintenance (e.g., routine washing to remove captured particles.) Optionally, the cleaned and purified ionized air may then pass through a humidifier 524 to warm and humidify the air. In some cases, the ground element 522 may be integrated with the humidifier, such that a component of the humidifier serves as the ground element. The pressurized humidified ionized cleaned/purified air may then pass through the delivery tube 110 toward the mask or other patient respiratory interface. Optionally, the flow of humidified cleaned ionized air may pass through a supplemental or secondary ionizer, e.g., ionizer 101-B, that may be located near or within the mask or patient interface 108. Such a supplemental ionizer, being more proximate to the user, may help to ensure that the gas is charged (e.g., negatively) for patient inhalation.

In some cases, the delivery conduit or delivery tube 110 of a flow generator may be configured to promote flow of charged gas for patient inhalation (e.g., reduce flow impedance) and may thereby help to permit charged air to be inhaled by the user/patient. For example, the material of the conduit may be chosen so that its flow surface (e.g., interior conduit wall) may have a shear to repel the charged treatment gas. For example the walls of the conduit may be formed of a material that has a charge the same as the charged treatment gas to repel the charged treatment gas and reduce resistance through the conduit. In the case of anion gas therapy, the conduit may be formed of a material having a negative charged state. For example, the delivery conduit may be formed of polyurethane, polyethylene, polypropylene, vinyl (pvc), silicon, teflon and/or silicone such as silicone rubber.

The use of material forming charged walls of the conduit also prevents the walls of the conduit from having the charged treatment gas from attaching or grounding upon the walls of the conduit. This arrangement may enable the secondary ionizer 101-B to be located closer to the flow generator, such as at the flow generator end of the conduit.

Still further, in some cases, the delivery conduit may employ one or more elements to more actively charge the conduit to repel the charged gas from attaching to the walls of the conduit for a reduced flow impedance. For example, for an anion gas therapy, the delivery tube 110, such as the example illustrated in FIG. 7, may employ one or more tube sheet anodes 711, such as anodes formed cylindrically around an exterior or interior of the delivery conduit surface. Such tube sheet anodes may be positioned in series along the tube length to negatively charge the conduit surface of the flow path.

Figure 7:
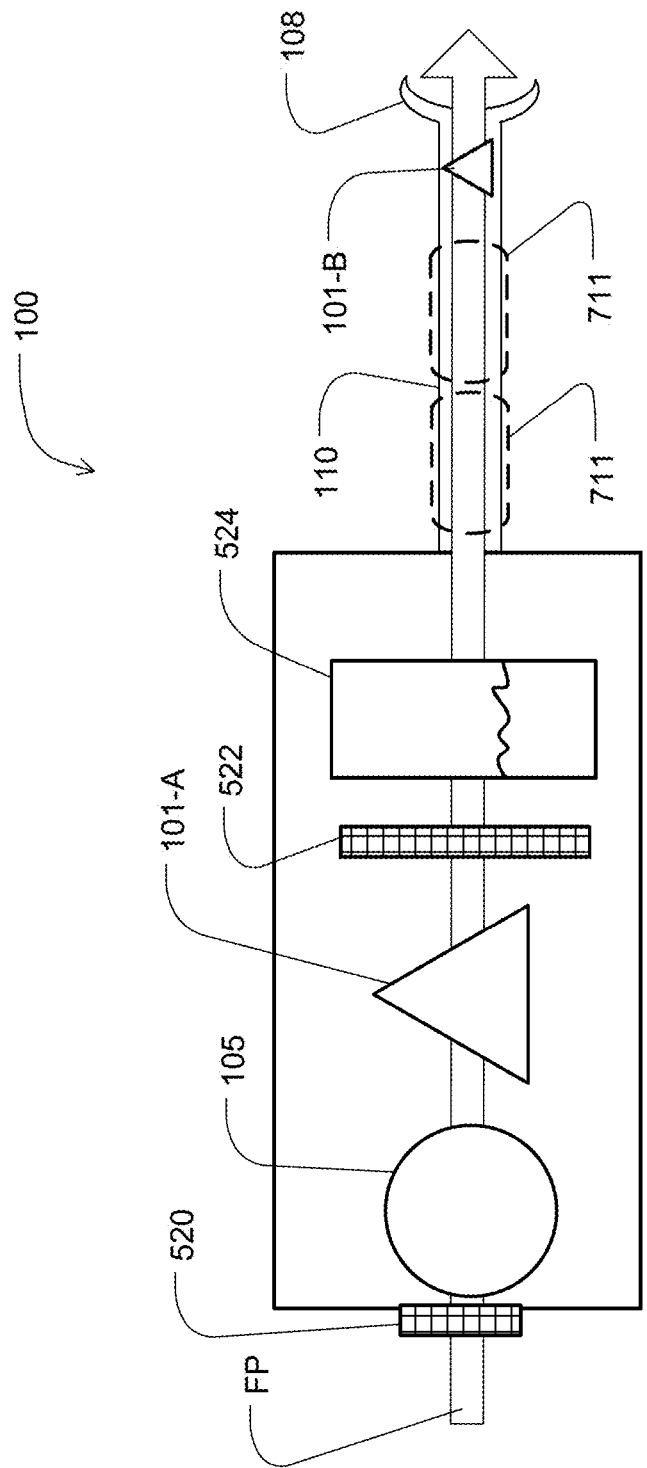
FIG. 7 is a diagram of an example ionization therapy device with active charging element to promote gas transfer through the delivery conduit.

In all other aspects the device 100 illustrated in FIG. 7 is similar to that shown in FIG. 5. The device may include an optional filter 520, a blower 105 and a first ionizer 101-A that are controlled by a controller (not shown), a ground element 522, such as a grounded filter or electret filter and optionally a humidifier 524 to warm and humidify the air. In some cases, the ground element 522 may be integrated with the humidifier as described above. The pressurized humidified ionized cleaned/purified air may then pass through the delivery tube 110 comprising the one or more tube sheet anodes 711 toward the mask or other patient respiratory interface. Optionally, the flow of humidified cleaned ionized air may pass through a supplemental or secondary ionizer, e.g., ionizer 101-B, that may be located near or within the mask or patient interface 108.

As previously mentioned, the ionization therapy device 100 can be configured to generate a respiratory flow or pressure treatment toward or in a patient respiratory interface in many different therapy forms (e.g. high flow treatment, CPAP, Bi-level pressure treatment, etc.). In some such cases, it may do so without a blower. For example, one or more ion generators may serve as a solid-state flow generator (FG) to propel a flow of breathable gas. In such a case, the controller may control operation of the ion generator(s) to regulate or control (e.g., increase or decrease) a level of flow or pressure of gas induced by ionization of the gas at or near the anodes or cathodes of the ion generator. As such, the flow generator of a respiratory apparatus may be implemented substantially without moving components. Moreover, the power consumption of such a device may be generally lower than power consumed for a typical blower (e.g., motor and impeller) implemented flow generator. For example, such a device when implemented for a high flow air therapy (HFAT) may have a much lower power consumption compared to a typical blower-implemented flow generator. Similarly, such a device when implemented for a continuous positive airway pressure (CPAP) may have a better/lower power consumption when compared to a typical blower-implemented flow generator. Generally, when compared to traditional blower control circuit configurations, such power consumption reductions for the solid state flow generators may be achieved through significantly lower current use circuits, though with potentially higher voltage use. The lower power consumption may include a reduction in power consumption of more than 50%, 60%, 70%, 80% or 90% of the power usage compared to a typical blower implemented flow generator.

In some cases, the ionization therapy device may be configured to be portable, for instance suitable to be worn or carried by the patient. Since the ionization therapy device may consume lower power than traditional blower-implemented flow generator, it may be particularly suited for a portable configuration. In one arrangement of a portable configuration, the ionization therapy device may include a disposable ground element. In one arrangement, the disposable ground element may be integrally constructed with a delivery tube to form a disposable delivery tube. Alternatively, the disposable ground element may be removable from the ionization therapy device, such as removable from the delivery tube, or removable from the body of the ionization therapy device, so that the disposable ground element may be replaced as required.

Over the course of operation of the ionization therapy device, particulates or contaminants may accumulate on the disposable element/component and necessitate replacement at periodic interval. In some forms, the ionization therapy device may include an indicator to improve identification of a disposable component that is due for replacement, such as the disposable ground element or the disposable delivery tube. One such indicator may include a color element to increase contrast between conditions of disposable components, (e.g., between a 'new' condition and a 'to be replaced' condition for the disposable component. For example, the disposable ground element may include an indicator surface that is visible to the patient or the caregiver that is colored in a bright color such as yellow. Over the course of operation of the ionization therapy device, accumulation of particulates on the indicator surface may change its appearance to indicate that the disposable ground element is due for replacement. The ionization therapy device may also comprise a color reference guide in some cases for the patient to use for comparison to the indicator surface. Alternatively, the indicator may include a light sensor configured to determine the condition of the disposable component. In one form, the light sensor may be configured to receive light from a light source that is reflected from a surface of the disposable element. The magnitude or quality of light received by the light sensor may vary according to the condition of the disposable component. In one arrangement, as the disposable component, such as the disposable ground element, collects contaminants, the amount of light captured by the light sensor may decrease, and this may be indicated by a decrease in the lux level of light captured by the light sensor. In another arrangement, the light captured by the light sensor may change in color, such as from a red light captured from a 'new' ground element, to a predominantly dull white light captured from a 'to be replaced' ground element. In such arrangements, the light sensor may be configured to output a signal indicating the amount of light captured and/or the condition of the disposable component. A controller may also be configured in conjunction to receive the signal from the light sensor and indicate to the patient that the disposable component may require replacement.

Optionally, in some cases a reminder of the need for replacement of the disposable component may be presented on a display (e.g., LCD) of the respiratory apparatus. For example, a visible message may be presented for a user to indicate that a ground element should be replaced. Such a message may be triggered by a processor of the apparatus, such as by timing use of the flow generator (or timing use of an ionizer(s)) with a timer or count down timer and triggering the reminder after a lapse of a predetermined amount of time. Such a timer may be manually reset by the user upon installation of the replacement component. In some cases, the reset may be triggered automatically by the respiratory apparatus upon detection of the replacement part (e.g., ground element). For example, the apparatus may detect the installation by detection of an identification tag such as a radio frequency identification tag (RFID) of the ground element. In some cases, the component may be detected by any of the identification technologies described in U.S. Pat. No. 7,913,689, the entire disclosure of which is incorporated herein by cross reference. Optionally, the presentation of the reminder may also or alternatively be triggered based on the evaluation involving the light sensor as previously described.

Figure 8:
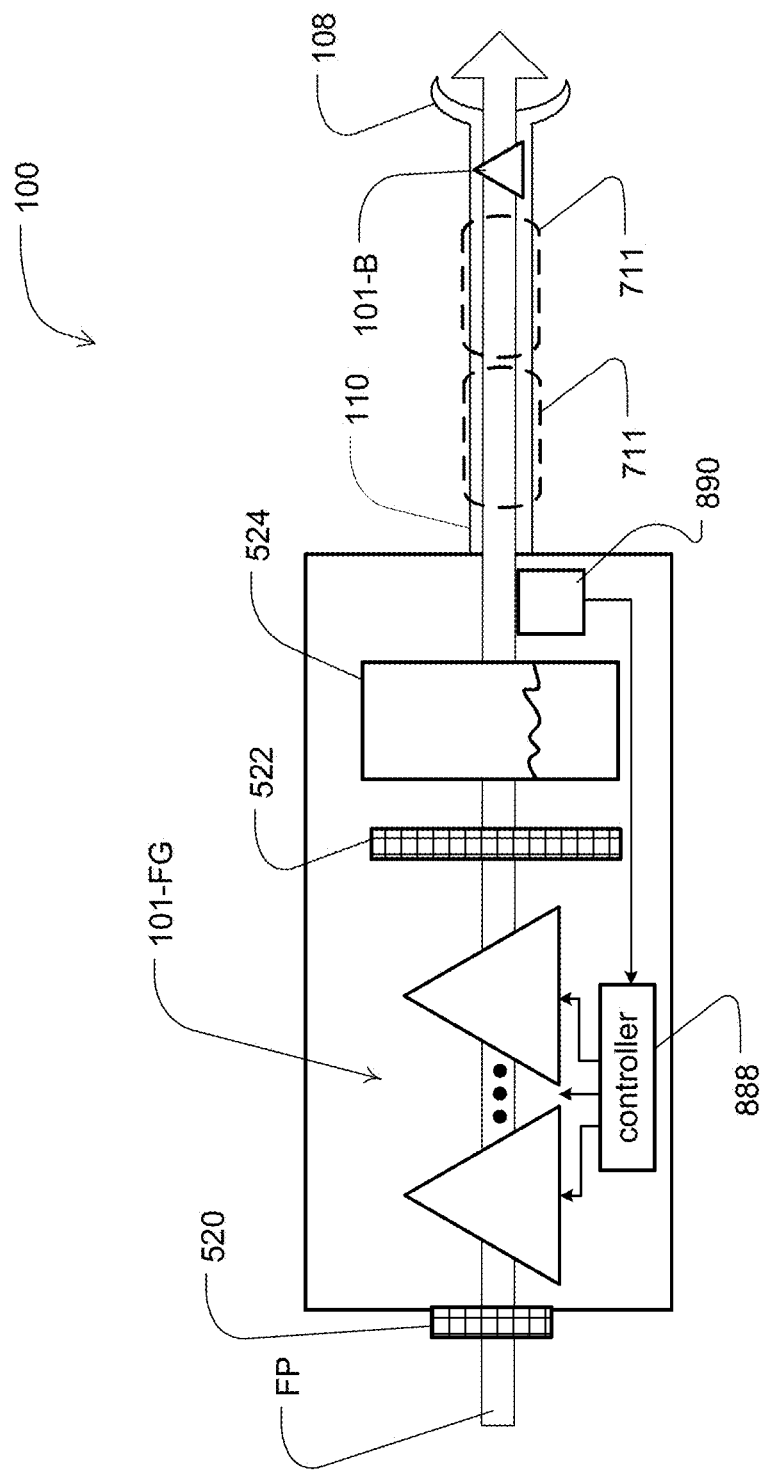
FIG. 8 is a diagram of an example ionization therapy device with a solid stage flow generator.

FIG. 8 shows an example flow path of a flow generator that may include a series of two or more ion generators along the flow path as illustrated. Selective activation or deactivation of the ion generators may be controlled to increase or decrease a flow of breathable gas generated within the flow path. For example, activation of a single ion generator may propel a low flow or low pressure level of breathable gas. By increasing the number of activated generators along the path, which can permit a pressure lock between each consecutive generator of the path, the flow (and thus, the pressure) propulsion may increase so as to implement a cascade acceleration effect.

As illustrated the device 100 of FIG. 8 may also include one or more of an optional filter 520, ground element 522, humidifier 524, tube sheet anodes 711 and/or a secondary ionizer 101-B in a similar arrangement to that described above in relation to FIGS. 5 and/or 7. The device is configured to deliver the supply of pressurized, optionally humidified, ionized gas to a mask or patient interface 108.

The ion generators may be coupled to heating elements to provide heated ionized air to the user. The heating elements and ion generators may be surrounded by a wicking material that is configured to hold a supply of water that is humidified by the heating elements resulting in the supply of a humidified heated ionized flow of air to the user. The wick and heating elements may be in the form of heating strips as described in United States Patent Application Publication No. 2010/0206308, filed Jan. 10, 2010, the entire disclosure of which is incorporated herein by reference.

Control of the ion generators for such flow and/or pressure generation may be in a closed or open loop control configuration. For example, the generated flow by activation of the ion generator(s) may be responsive to measured system or patient characteristics from one or more sensor(s) 890, such as any of the sensors previously mentioned or for example, flow and/or pressure sensors in a control loop utilizing flow and/or pressure measures. In some such cases, the number of ion generator activations by a controller 888 may increase or decrease until a measured characteristic (e.g., a measured flow signal or measured pressure signal) meets a target (e.g., set or desired target flow value or pressure value). Changes to such flow or pressure may be made in accordance with any known flow or pressure treatment control scheme based on detected patient characteristics such as from an analysis of a patient respiratory flow signal. In some of these examples, the flow generator may selectively produce varying levels of flow or pressure by selectively activating different numbers of ion generators. However, in some implementations, the flow propulsion to a respiratory interface that is generated from the group of ion generators may be varied by varying an exhaust area, such as with an electro-mechanical exhaust vent or valve of the flow generator or respiratory interface, while maintaining the activation of the ion generators to be relatively constant.

Figure 9B:
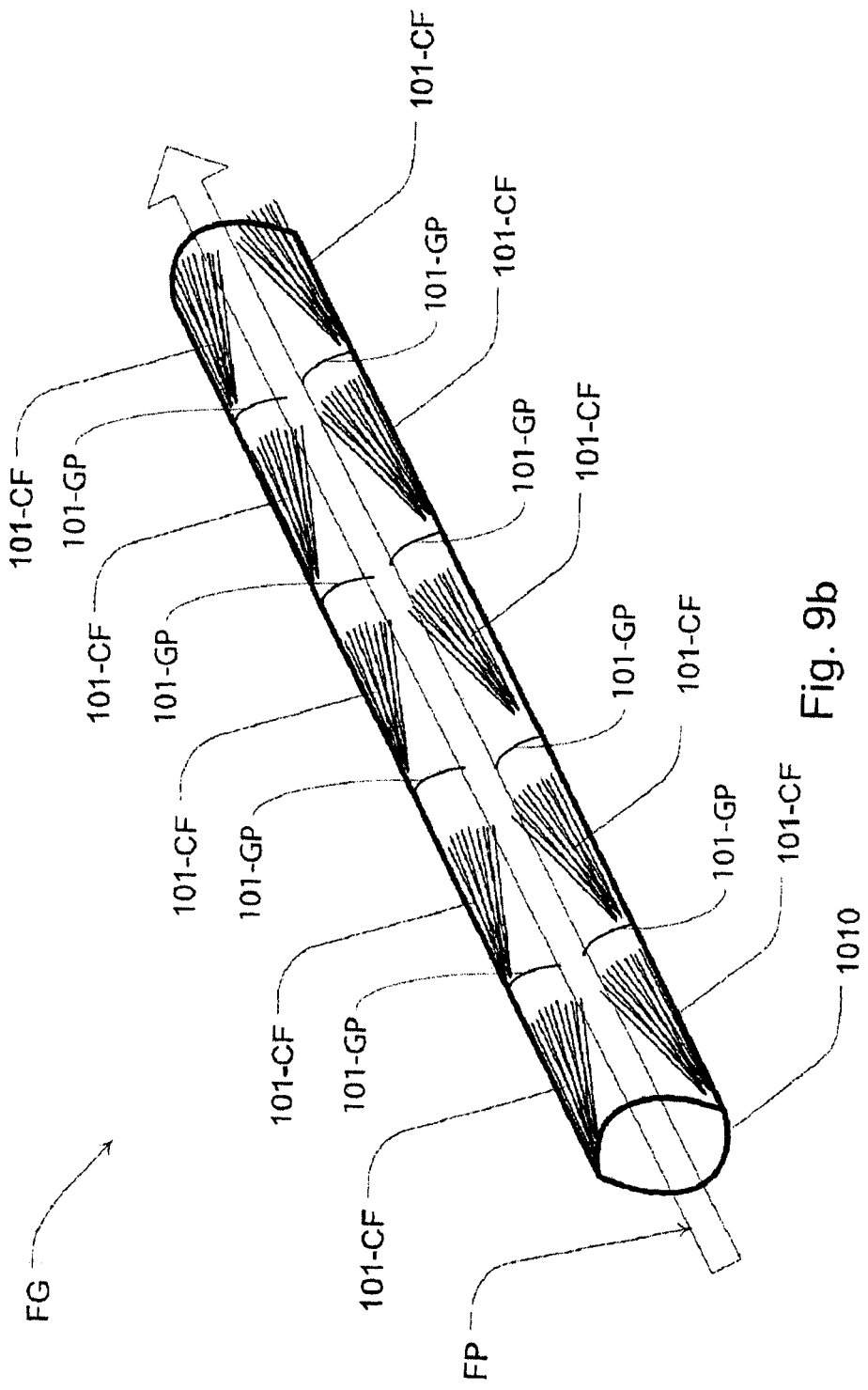

Some example series implementations are illustrated in the ionization flow generators of FIGS. 9a, 9b and 10. In FIG. 9a, sets of carbon fiber brush ionizers 101-CF may serve as a flow generator (FG). According to another instance of the present technology, each carbon fiber brush ionizer 101-CF may be further matched to a corresponding ground plane 101-GP such as that shown in FIG. 9b. In this arrangement, the direction between the carbon fiber brush ionizer 101-CF and the corresponding ground plane 101-GP may define the direction of ionization. This arrangement may allow for improved consistency in the direction of ionization allowing improved control of the direction of propulsion of ionized air.

Preferably, the ground plane 101-GP is sufficiently close to the corresponding ionizer, such as 101-CF, to allow ionization to occur. Conversely, the ground plane 101-GP should be sufficiently far from any other ionizers 101-CF in order to prevent any unwanted ionization from occurring between any other pairs of ground planes and ionizers. One example of a suitable arrangement of a ground plane 101-GP may be a conductive plate, for example made of a ferrous metal, although other materials and arrangements may be suitable. In some cases, the ground plane 101-GP may be connected to, or integrally formed with, a metallic component of the flow generator FG such as the housing.

In FIG. 10, sets of honeycomb ionizers 101-HC may serve as a flow generator (FG). By selectively increasing the number of ionizers that are activated in the flow conduit, such as by a controller, an increase in flow in the flow path (FP) may be induced. In some cases, the fiber brushes or honeycomb ionizers 101-HC may be formed within or along a flow path, such as a conduit 1010. For example, as illustrated in FIG. 9a an initial set of brushes may be grouped so as to surround a flow path through which a flow of air may be generated. Additional sets may then be serially configured further up the flow path in the direction of the arrow of flow path (FP). In the example of FIG. 10 individual honeycomb cells are serially aligned along the flow path. However, in some cases, each such cell may be formed by a honeycomb array of ionizer cells through which the flow of ionized air may be generated.

Figure 11:
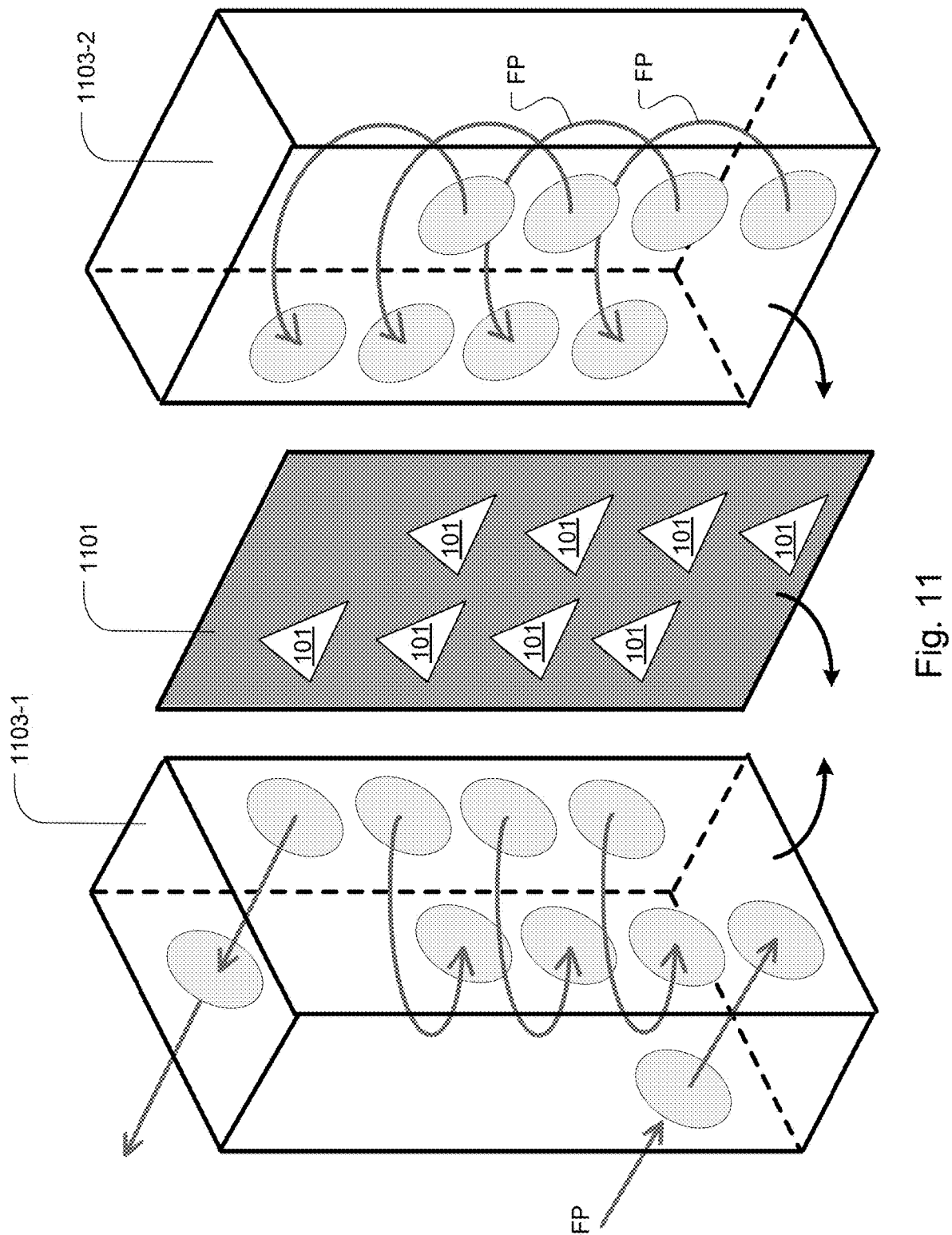
FIG. 11 is an illustration of example components of an ionization flow generator formed with a helical flow configuration.
Figure 12:
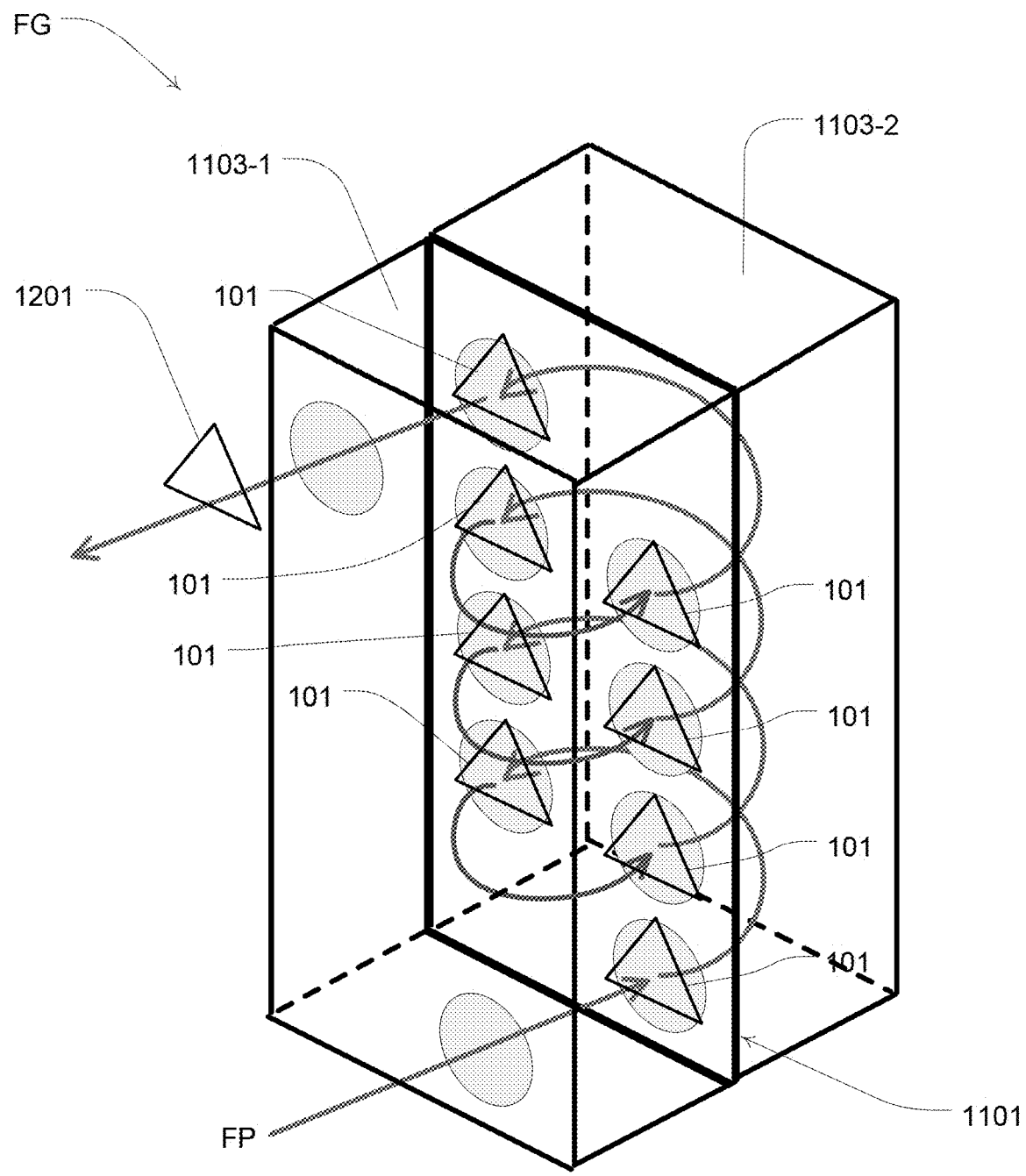
FIG. 12 is an illustration of the assembled components of the generator of FIG. 11.

In the ionizer/flow generator examples of FIGS. 11-14, a series of ionizers may be formed in a grid or sheet configuration with a helical or spiral flow configuration. Such a configuration may permit extending of the flow path length for flow acceleration via multiple ionizers while minimizing layout space. For instance, each ionizer 101 may have its cathode and anode arranged to accelerate the flow of breathable gas in a particular direction, such as the direction of ionization. For example, as illustrated in FIG. 11, one or more ionizer sheets 1101, with flow passages there through for a plurality of ionizers 101, may be coupled between first and second, flow structures, such as flow blocks 1103-1, 1103-2. The flow blocks may employ conduits or flow paths to route flow sequentially through the plurality of ionizers of the ionizer sheet 1101. For example, the flow conduits or paths of the first and second flow structures may be combined on opposing sides of the ionizer sheet 1101 as illustrated in FIG. 12 so as to form a helical or spiral flow path (FP) sequentially through each of the ionizers 101. Although the ionizer sheet 1101 is illustrated as a discrete component, in some examples one or more may be integrated with either or both of the block structures, such as on a surface thereof such as in the example of FIGS. 13A, 13B 14A and 14B. Similarly, in some cases, ionizers may be located spirally, rather than in a common plane of the sheet, along a spiral or helical flow path. Moreover, although the helical flow path is illustrated with block structures, it will be understood that such pathways may be implemented with simple conduits or tubes making the appropriate series of connections with the ionizers.

Figure 15:
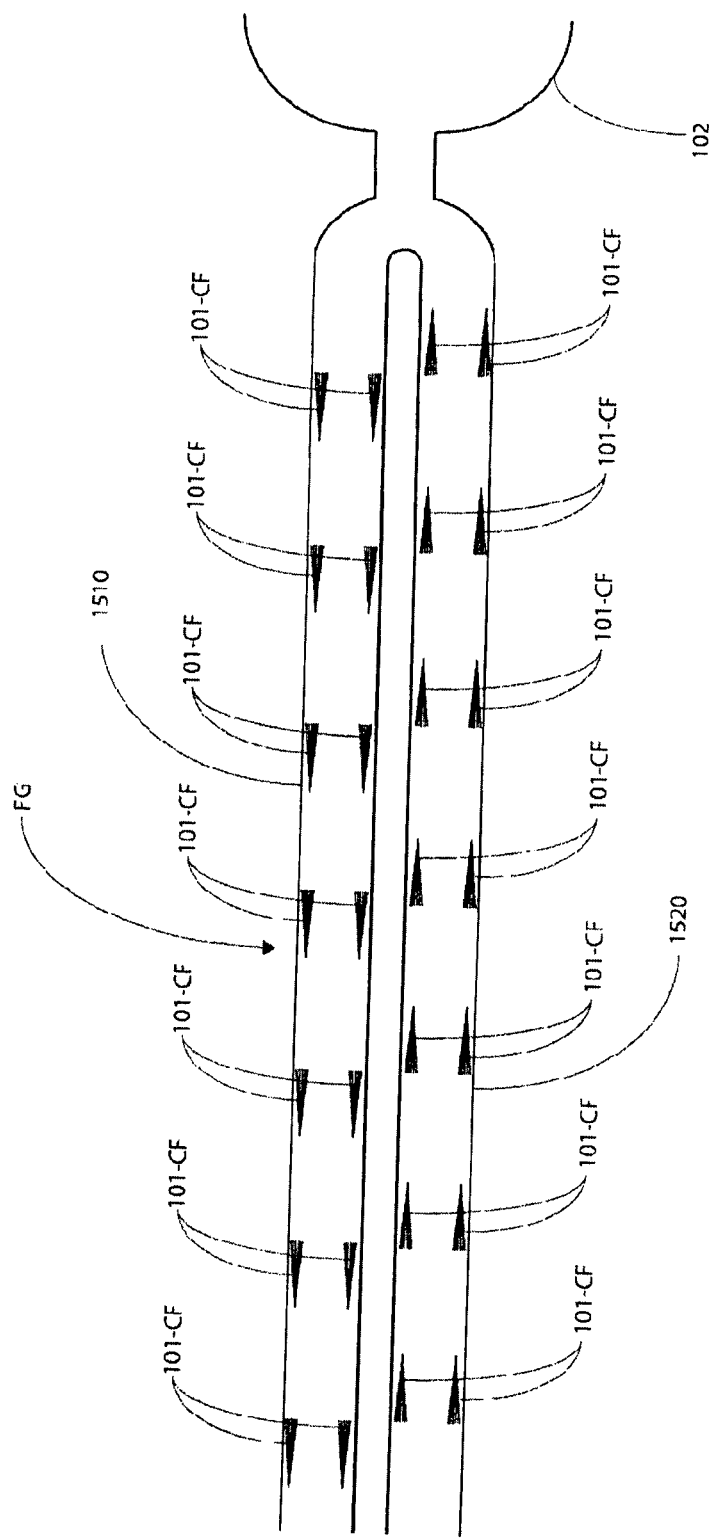
FIG. 15 is an illustration of a patient interface and a flow generator including a dual-limb delivery conduit that comprises ionizers.

In another arrangement according to the present technology, ionizers may be used in a delivery conduit which comprises multiple tubes, such as a dual-limb air delivery conduit shown in FIG. 15. The air delivery circuit shown in FIG. 15 includes an inspiratory limb 1510 comprising carbon fiber brush ionizers 101-CF arranged in one orientation, and an expiratory limb 1520 comprising carbon fiber brush ionizers 101-CF arranged in the opposite orientation. The carbon fiber brush ionizers may be arranged to propel the inspiratory flow or the expiratory flow along a desired direction.

Figure 16A:
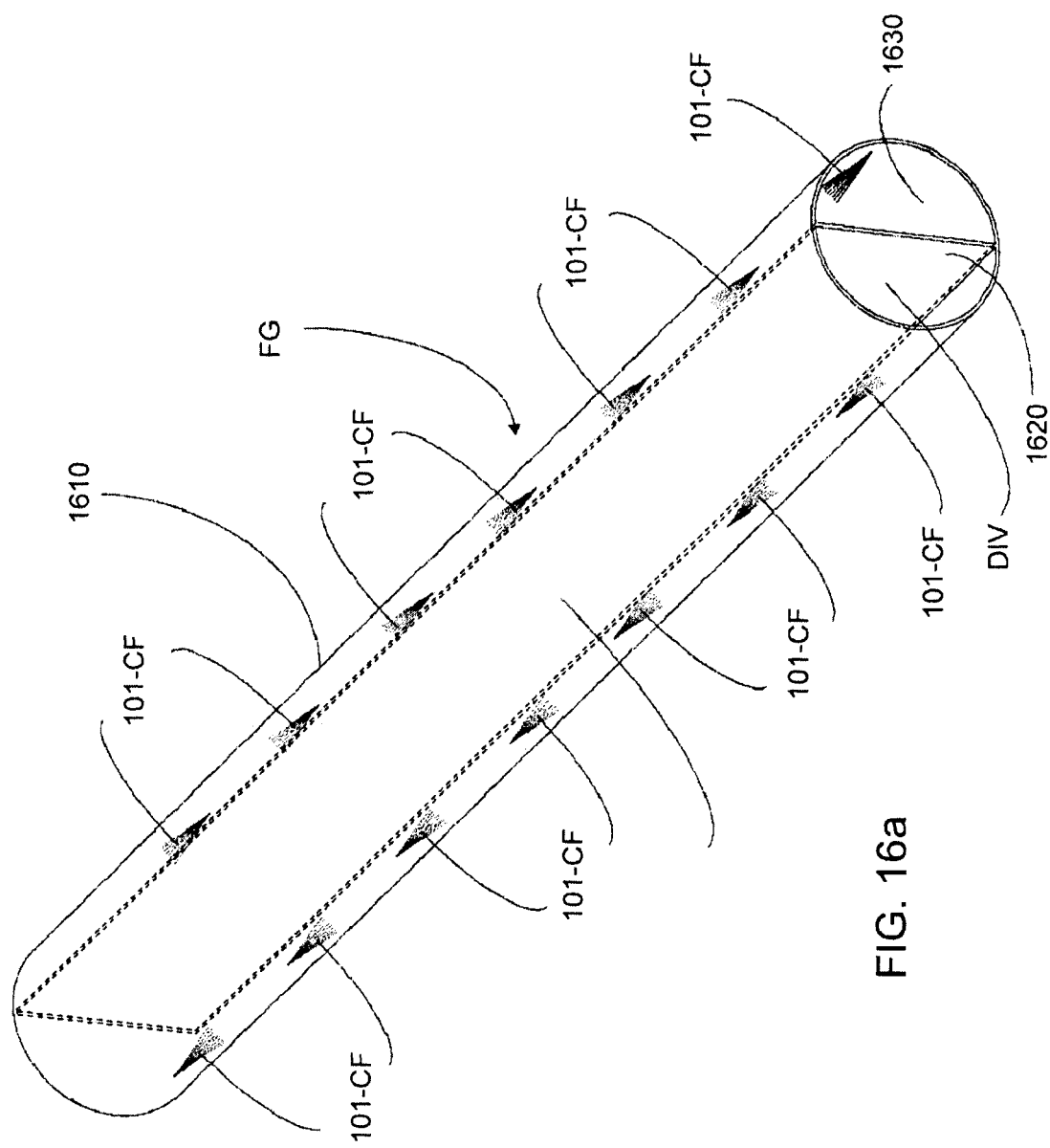
FIGS. 16a and 16b are illustrations of a flow generator comprising a delivery conduit having an inspiratory channel with ionizers, an expiratory channel with ionizers and a divider, such as a divider configured as a plate.

In a yet another arrangement, ionizers may be used in an air delivery conduit which comprises multiple channels in a tube as shown in FIG. 16a-18. FIG. 16a and FIG. 16b show an arrangement of the conduit formed as a tube 1610 with a divider DIV. In some cases, the divider DIV may be inserted to sealingly engage with the tube 1610 to create two or more channels, such as an inspiratory channel 1620 and an expiratory channel 1630. In other cases, the divider DIV may be integrally formed with the tube 1610.

Figure 16B:
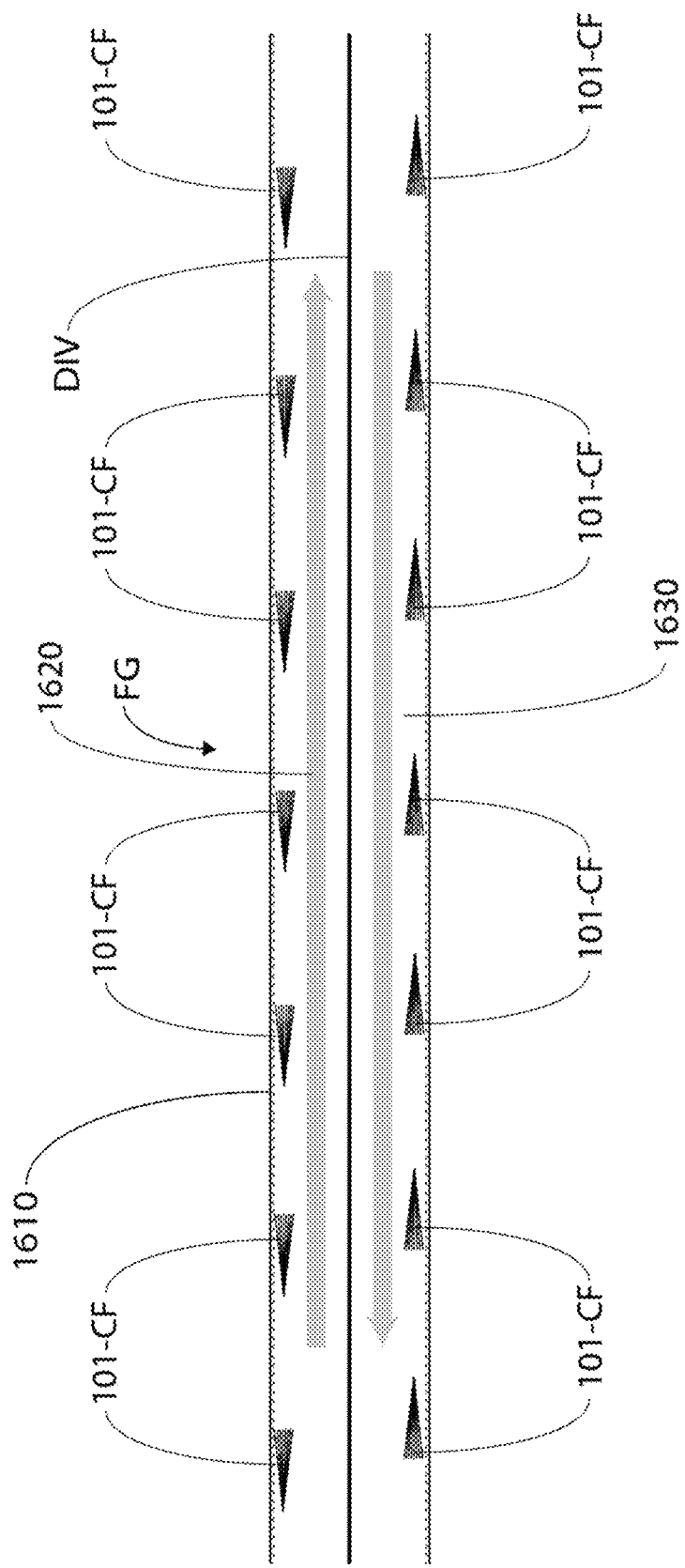

The inspiratory channel 1620 and/or the expiratory channel 1630 may comprise a set of ionizers, such as carbon fiber ionizers 101-CF as shown in FIGS. 16a and 16b. The ionizers 101-CF may be configured to accelerate the flow of gas in the desired direction as previously described. According to some arrangements, the divider DIV may be configured as a ground element, or a part thereof, for the inspiratory channel 1620 and/or the expiratory channel 1630. This may be potentially advantageous by reducing complexity of the device, and potentially also reduce manufacturing costs. In some cases, the divider DIV may be removably coupled to the tube 1610 to facilitate maintenance as described above.

Figure 17:
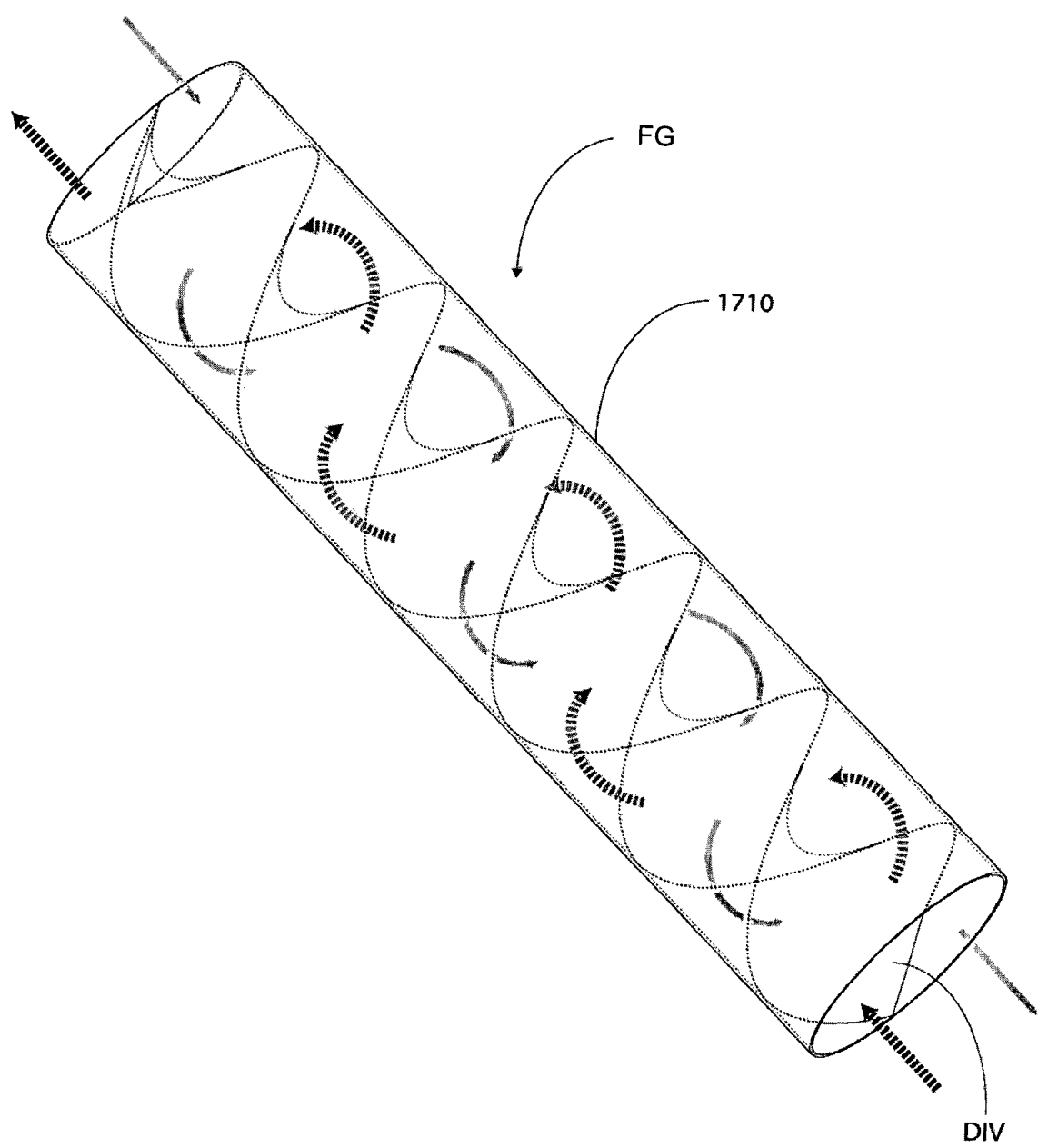
FIG. 17 is an illustration of a flow generator comprising a delivery conduit having an inspiratory channel with ionizers, an expiratory channel with ionizers and a divider, such as a divider configured in a helical arrangement.

FIG. 17 shows an arrangement according to the present technology where the divider DIV is arranged helically in a cylindrical delivery tube 110. In this arrangement, the ionizers such as carbon fiber brush ionizers 101-CF may be configured along the walls, and arranged in concert with the helical divider DIV to form a volute which may further increase flow velocity, for instance by using the helical divider DIV as a ground element or a part thereof.

It should also be understood that the number of delivery conduits or channels, as well as their flow directions, may be varied while taking advantage of the present technology. For instance, the air delivery conduit and divider arrangement shown in FIG. 17 may be used to provide a flow of breathable gas travelling in only one direction, if so desired.

Figure 18:
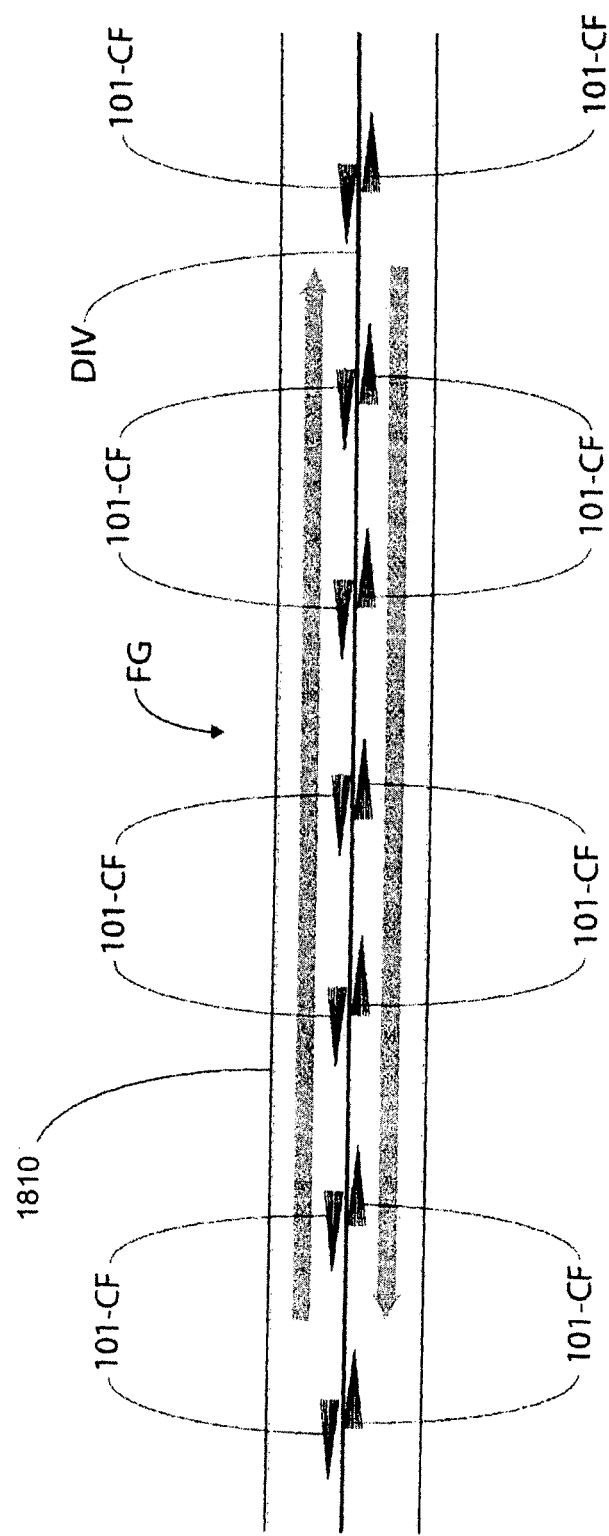
FIG. 18 is an illustration of a flow generator comprising a delivery conduit having an inspiratory channel, an expiratory channel with ionizers and a divider. The ionizers may be arranged on both sides of the divider.

In some cases, the flow generator FG may further comprise a humidifier. According to one arrangement, the flow generator FG may further comprise a wick to humidify the inspiratory flow. The divider may be arranged to incorporate one or more wicking strips and ancillary components, for example similar to those described in PCT Application publication number WO/2009/015410, the entire contents of which is incorporated herein by reference. Additionally, such a delivery conduit may be arranged to incorporate the ionizers in any number of arrangements. For instance, as shown in FIG. 18, the ionizers, 101-CF may be arranged on both sides of a divider DIV, and the tube 1810 may be used as the ground element. In another example, a part or the entirety of the divider DIV may also include an exchanger for heat and/or moisture, for example as disclosed in PCT Application number PCT/AU2012/001382, the entire contents of which is incorporated herein by reference.

While the solid state ionizer flow embodiments described herein may be suitable for generation of a flow of ionized air for an ionized air therapy to be delivered to the respiratory system of a patient or user, in some embodiments the ionized airflow generated may be neutralized for delivery to a patient or user substantially without an ion therapy. For example, a ground element or other neutralizing element 1201 may be implemented at or following the flow output end of the ion flow generator to deionize the breathable gas. For example, in a case of an anion flow generator, one or more cathodes at the end of the series of anion generators may be included to neutralize the air for patient or user inhalation. Thus, the solid state ion flow generator may be implemented for a pressure or flow treatment to a patient or user without providing significant ionized air therapy to the patient or user.

Example System Architecture

Figure 6:
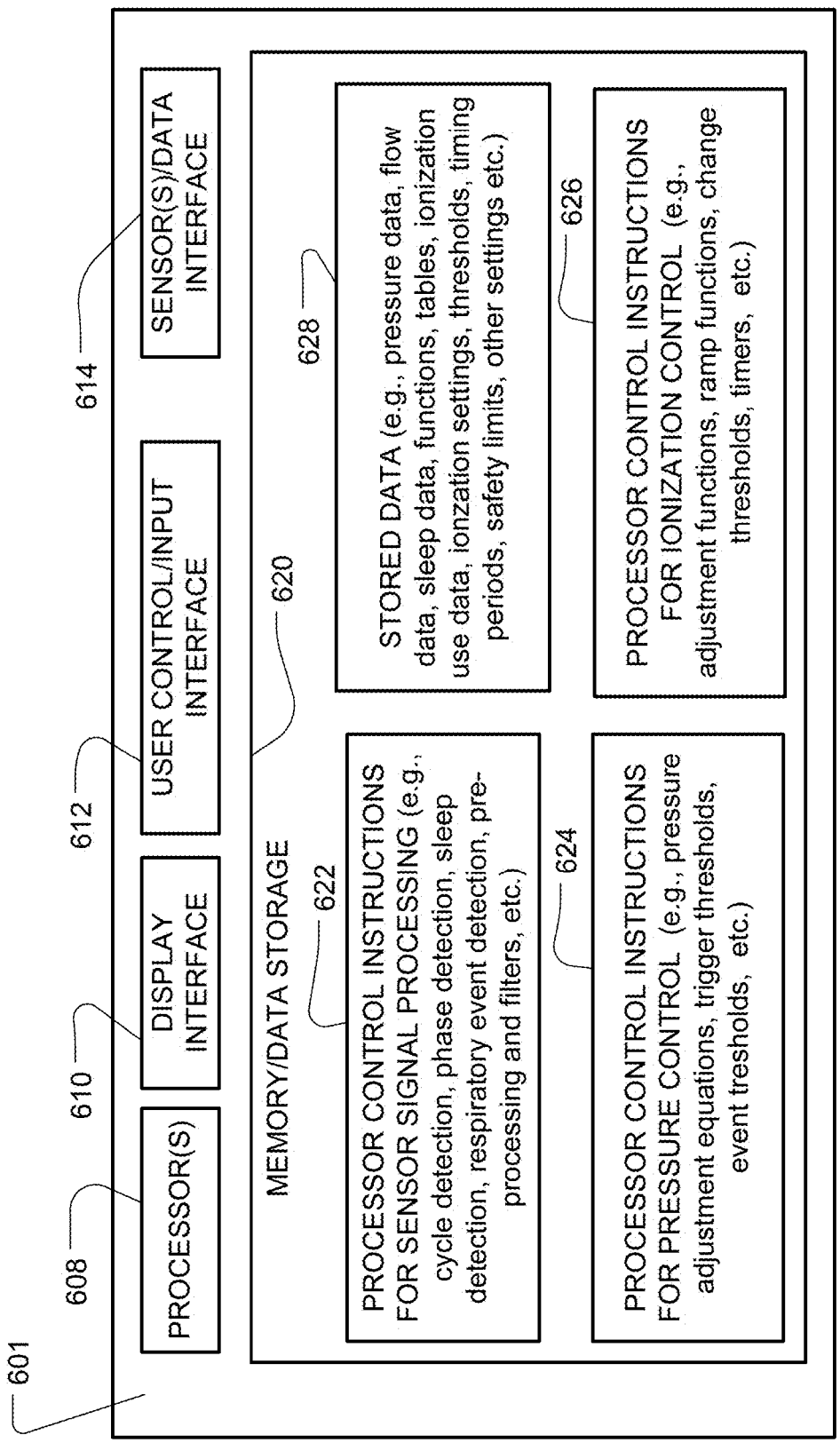
FIG. 6 is a block diagram of a controller for a respiratory ionization therapy apparatus including example components suitable for implementing the control methodologies of the present technology.

An example system architecture of a controller suitable for implementing the present pressure/flow and/or ionization therapy technology is illustrated in the block diagram of FIG. 6. In the illustration, the controller 601 for the ionization therapy device 100 may include one or more processors 608. The device may also include a display interface 610 to output pressure, event and/or ionization graphs (e.g., respiratory event vs. time curves, flow and/or pressure vs. time curves or ionization level vs. time curves, such as those as illustrated in FIGS. 3 and 4 or the like, etc.) as described herein such as on a monitor or LCD panel. A user control/input interface 612, for example, for a keyboard, touch panel, control buttons, mouse etc. may also be provided to activate or modify the control parameters or settings for the methodologies described herein. For example, these may be utilized for entering settings for ionization periods and ionization levels, safety limits, etc., and/or for activation of the initiation of one or more timed wake periods when a patient or user deems it necessary to fall or return to sleep during a session with the device. The device may also include a sensor or data interface 614, such as a bus, for receiving/transmitting data such as programming instructions, flow data, ionization data, pressure data, settings for ionization level modulation etc. The device may also typically include memory/data storage 620 components containing control instructions of the aforementioned methodologies (e.g., FIGS. 2-4). These may include processor control instructions for sensor signal processing (e.g., physiological characteristic detection (e.g., cycle detection, respiratory phase detection, sleep detection, arousal detection, sleep/awake state detection, blood oxygen saturation detection, respiratory event detection, apnea detection, hypopnea detection, hypoventilation detection, etc.,) pre-processing methods, filters, etc.) at 622 as discussed in more detail herein. They may also include processor control instructions for pressure/flow control and modulation (e.g., pressure adjustment equations, functions, and logic, trigger thresholds, event thresholds, etc.) at 624. They may also include processor control instructions for ionization modulation (e.g., ionization level adjustment equations, functions and logic, trigger thresholds, event thresholds, ramp functions, change thresholds, timers, timing thresholds, etc.) at 626. Finally, they may also include stored data 628, such as historic use data, for these methodologies such as pressure data, flow data, ionization data, sleep data, respiratory event data, functions, tables, ionization settings, thresholds, timing periods, safety limits, other settings, etc.)

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

The present technology advantageously provides a device that provides a clean supply of air even in polluted locations as the air is cleaned by the ionization and filtering process. Furthermore, by further ionizing the air supply clean, antiseptic and ion latching air can be supplied to the user. Thus, the device may be used in contaminated atmospheres to provide at least clean air either with or without other therapies being provided. The device may also provide a supply of clean air using a low power consumption.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" may be used herein, unless otherwise specified, the language is not intended to provide any specified order but merely to assist in explaining distinct elements of the technology. Furthermore, although process steps in the detection methodologies have been illustrated in the figures in an order, such an ordering is not required. Those skilled in the art will recognize that such ordering may be modified and/or aspects thereof may be conducted in parallel or synchronously. Moreover, although the features described herein may be utilized independently, various combinations thereof may be made in a respiratory pressure treatment apparatus. Other variations can be made without departing with the spirit and scope of the technology.

The invention claimed is:

1. A solid state airflow generator of a respiratory apparatus for generating a controlled supply of air, the solid state airflow generator comprising:
   a set of ionizers configured to propel a flow of air, the set of ionizers configured with a flow path adapted to couple with a user respiratory interface, wherein (a) the flow path is helical and the set of ionizers is arranged along the helical flow path or (b) the flow path comprises a conduit and the set of ionizers is arranged in a series in the conduit; and
   a controller coupled with the set of ionizers, the controller configured to selectively activate ionizers of the set of ionizers for propelling the flow of air, wherein the selectively activated ionizers propel the flow of air to generate a respiratory flow or pressure treatment toward or in the user respiratory interface.

2. The solid state airflow generator of claim 1 wherein the flow path includes a divider.

3. The solid state airflow generator of claim 2 wherein the divider separates two or more channels and wherein each channel includes a subset of the set of ionizers.

4. The solid state airflow generator of claim 3, wherein the channels comprise an inspiratory channel and an expiratory channel.

5. The solid state airflow generator of claim 2 wherein the divider is configured as a ground element.

6. The solid state airflow generator of claim 2 wherein the divider is arranged helically in a cylindrical delivery tube.

7. The solid state airflow generator of claim 2 wherein the solid state airflow generator propels the flow of air without a blower.

8. The solid state airflow generator of claim 2 wherein the solid state airflow generator propels the flow of air substantially without moving components.

9. The solid state airflow generator of claim 1 further comprising a sensor, wherein the controller is configured to activate a sub-set of the set of ionizers based on a signal generated from the sensor.

10. The solid state airflow generator of claim 9 wherein the sensor is a flow sensor, and wherein the controller is configured to selectively activate a sub-set of the set of ionizers based on a measure of flow from a signal from the flow sensor.

11. The solid state airflow generator of claim 9 wherein the sensor is a pressure sensor, and wherein the controller is configured to selectively activate a sub-set of the set of ionizers based on a measure of pressure from a signal of the pressure sensor.

12. The solid state airflow generator of claim 9 wherein the sensor is a pressure sensor, and wherein the controller is configured to selectively activate a sub-set of the set of ionizers based on a measure of pressure from a signal of the pressure sensor to control a delivery of a treatment pressure.

13. The solid state airflow generator of claim 1 wherein the selectively activated ionizers propel the flow of air to generate the respiratory flow.

14. The solid state airflow generator of claim 13 wherein the respiratory flow comprises a high flow treatment.

15. The solid state airflow generator of claim 1 wherein the selectively activated ionizers propel the flow of air to generate the pressure treatment.

16. The solid state airflow generator of claim 15 wherein the pressure treatment comprises a continuous positive airway pressure (CPAP) treatment.

17. The solid state airflow generator of claim 1 wherein the set of ionizers is arranged in a serial configuration in the flow path and wherein the controller selectively activates an increasing number of ionizers of the set of ionizers to increase propulsion of the flow of air.

18. The solid state airflow generator of claim 1 wherein the set of ionizers comprises an ionizer sheet.

19. The solid state airflow generator of claim 1 wherein the flow path is helical and the set of ionizers is arranged along the helical flow path.

20. The solid state airflow generator of claim 1 further comprising a neutralizer, the neutralizer configured to deionize the propelled flow of air of the flow path.

21. The solid state airflow generator of claim 1 wherein the set of ionizers comprises a plurality of carbon fiber brush ion generators.

22. The solid state airflow generator of claim 1 wherein the set of ionizers comprises a plurality of honeycomb cell ion generators.

23. The solid state airflow generator of claim 2 wherein the divider is configured for removably coupling within the conduit.

24. The solid state airflow generator of claim 1 wherein the flow path comprises the conduit and the set of ionizers is arranged in a series in the conduit.

25. A solid state airflow generator of a respiratory apparatus for generating a controlled supply of air, the solid state airflow generator comprising:
   a set of ionizers configured to propel a flow of air, the set of ionizers configured with a flow path adapted to couple with a user respiratory interface, wherein (a) the flow path is helical and the set of ionizers is arranged along the helical flow path or (b) the flow path comprises a conduit and the set of ionizers is arranged in a series in the conduit; and
   a controller coupled with the set of ionizers, the controller configured to selectively activate ionizers of the set of ionizers for propelling the flow of air, wherein the set of ionizers is arranged in a serial configuration in the flow path and wherein the controller selectively activates an increasing number of ionizers of the set of ionizers to increase propulsion of the flow of air.

* * * * *